United States Patent
Yamada et al.

(10) Patent No.: US 10,113,966 B2
(45) Date of Patent: Oct. 30, 2018

(54) BLOOD ANALYZER, DIAGNOSTIC SUPPORT METHOD, AND NON-TRANSITORY STORAGE MEDIUM

(71) Applicant: Sysmex Corporation, Kobe-shi, Hyogo (JP)

(72) Inventors: Kazuhiro Yamada, Kobe (JP); Kazuhiro Sasaki, Kobe (JP); Seiichiro Tabata, Kobe (JP); Takeshi Yamamoto, Kobe (JP)

(73) Assignee: SYSMEX CORPORATION, Hyogo (JP)

(*) Notice: Subject to any disclaimer, the term of this patent is extended or adjusted under 35 U.S.C. 154(b) by 154 days.

(21) Appl. No.: 14/836,275

(22) Filed: Aug. 26, 2015

(65) Prior Publication Data

US 2016/0061732 A1 Mar. 3, 2016

(30) Foreign Application Priority Data

Aug. 28, 2014 (JP) ................. 2014-173923
Mar. 27, 2015 (JP) ................. 2015-065590

(51) Int. Cl.
*G01N 33/00* (2006.01)
*G01N 21/64* (2006.01)
(Continued)

(52) U.S. Cl.
CPC ..... *G01N 21/6428* (2013.01); *G01N 21/6486* (2013.01); *G01N 33/49* (2013.01);
(Continued)

(58) Field of Classification Search
None
See application file for complete search history.

(56) References Cited

U.S. PATENT DOCUMENTS

2005/0219527 A1* 10/2005 Ikeuchi .............. G01N 15/1459
356/339
2010/0240055 A1* 9/2010 Godefroy ............. G01N 33/537
435/6.12
(Continued)

FOREIGN PATENT DOCUMENTS

CN 2209331 Y 10/1995
CN 101236158 A 8/2008
(Continued)

OTHER PUBLICATIONS

Devanesan, S. et al., "Fluorescence Spectral Classification of Iron Deficiency Anemia and Thalassemia", *Journal of Biomedical Optics, SPIE—International Society for Optical Engineering*, vol. 19, No. 2, Feb. 2014, pp. 027008-1 to 027008-5.
(Continued)

*Primary Examiner* — Jill A Warden
*Assistant Examiner* — Brittany I Fisher
(74) *Attorney, Agent, or Firm* — Brinks Gilson & Lione

(57) ABSTRACT

A blood analyzer comprises a light source unit configured to irradiate light on a measurement sample prepared from blood, a fluorescent light detecting unit configured to detect auto-fluorescence produced by red blood cells in the measurement sample which is irradiated by light, an information processing unit configured to obtain auto-fluorescence information related to red blood cells which produce auto-fluorescence detected by the fluorescent light detecting unit. The information processing unit is configured to make a determination regarding anemia based on the auto-fluorescence information.

19 Claims, 30 Drawing Sheets

(51) Int. Cl.
*G01N 33/80* (2006.01)
*G01N 33/90* (2006.01)
*G01N 33/49* (2006.01)

(52) U.S. Cl.
CPC ............ *G01N 33/80* (2013.01); *G01N 33/90* (2013.01); *G01N 2021/6439* (2013.01)

(56) References Cited

U.S. PATENT DOCUMENTS

| | | | |
|---|---|---|---|
| 2010/0273168 A1* | 10/2010 | Krockenberger | G01N 15/00 435/6.12 |
| 2011/0178716 A1* | 7/2011 | Krockenberger | G01N 15/147 702/19 |
| 2014/0273064 A1* | 9/2014 | Smith | G01N 33/57438 435/29 |

FOREIGN PATENT DOCUMENTS

| | | |
|---|---|---|
| CN | 101713728 A | 5/2010 |
| CN | 102822670 A | 12/2012 |
| CN | 102933964 A | 2/2013 |
| EP | 1 574 839 A1 | 9/2005 |
| JP | 11-326315 A | 11/1999 |
| JP | 2008-175807 A | 7/2008 |
| JP | 2011-185841 A | 9/2011 |
| WO | WO 2009/136570 A1 | 11/2009 |

OTHER PUBLICATIONS

Nagababu, E. et al., "Iron-Deficiency Anemia Enhances Red Blood Cell Oxidative Stress", *Free Radical Research*, vol. 42, No. 9, 2008, pp. 824-829.

Riley, R. et al., "Reticulocyte Enumeration: Past & Present", *Laboratory Medicine*, vol. 32, No. 10, Oct. 2001, 10 pages.

* cited by examiner

BLOOD ANALYZER, DIAGNOSTIC SUPPORT METHOD, AND NON-TRANSITORY STORAGE MEDIUM

CROSS REFERENCE TO RELATED APPLICATIONS

This application claim priority from prior Japanese Patent Application No. 2014-173923, filed on Aug. 28, 2014, entitled "BLOOD ANALYZING METHOD, BLOOD ANALYZER, AND PROGRAM" and prior Japanese Patent Application No. 2015-065590, filed on Mar. 27, 2015, entitled "BLOOD ANALYZING METHOD, BLOOD ANALYZER, AND PROGRAM", the entire contents of which are incorporated herein by reference.

FIELD OF THE INVENTION

The present invention is related to a blood analyzer, diagnostic support method, and computer program for supporting the diagnosis of anemia using a measurement sample prepared from blood.

BACKGROUND

Iron-deficiency anemia (IDA) and thalassemia are known as ailments of microcytic anemia. Among these, iron deficiency anemia is said to account for about 50% of anemias.

There are blood cell counting devices which classify the blood cells contained in the blood collected from a patient, and count the number of blood cells of each type. Japanese Laid-Open Patent No. 11-326315 discloses a method of differentiating thalassemia and iron deficiency anemia using measurement values of CBC items, which are basic measurement items in blood cell counting devices.

Since iron deficiency anemia has test values similar to those of thalassemia, it is difficult to improve the differentiation accuracy of iron deficiency anemia and thalassemia by differentiation methods using measurement values of CBC items. Therefore, further improvement of anemia differentiation accuracy is desirable.

SUMMARY OF THE INVENTION

The blood analyzer of a first aspect of the present invention is provided with a light source unit, fluorescent light detecting unit, and information processing unit. The light source unit irradiates light on a measurement sample prepared from blood. The fluorescent light detecting unit detects auto-fluorescence produced by the red blood cells in the measurement sample which has been irradiated by light. The information processing unit obtains the auto-fluorescence information related to the red blood cells which give off the auto-fluorescence detected by the fluorescent light detecting unit, and makes a determination related to anemia based on the auto-fluorescence information.

The diagnostic support method of iron deficiency anemia of a second aspect of the present invention includes irradiating light on a measurement sample prepared from blood, detecting the auto-fluorescence from the red blood cells in the irradiated measurement sample, obtaining auto-fluorescence information related to the red blood cells which give off the detected auto-fluorescence, and making a determination related to anemia based on the auto-fluorescence information.

The non-transitory storage medium of a third aspect of the present invention stores a computer program for causing a computer to execute: a step of obtaining auto-fluorescence information related to red blood cells that produce auto-fluorescence based on the results of detecting auto-fluorescence produced by red blood cells in the measurement sample when light is irradiated on a measurement sample prepared from blood, and a step of making a determination related to anemia based on the auto-fluorescence information.

The present invention can improve the accuracy of the determination of anemia.

DETAILED DESCRIPTION OF THE PREFERRED EMBODIMENTS

First Embodiment

In the first embodiment, the blood analyzer is described in terms of detecting auto-fluorescence from red blood cells contained in a blood sample, and making a determination related to iron deficiency anemia and thalassemia. The blood analyzer detects each type of blood cells contained in blood by a flow cytometric method, and counts the detects blood cells.

Blood Analyzer Structure

Figure 1:
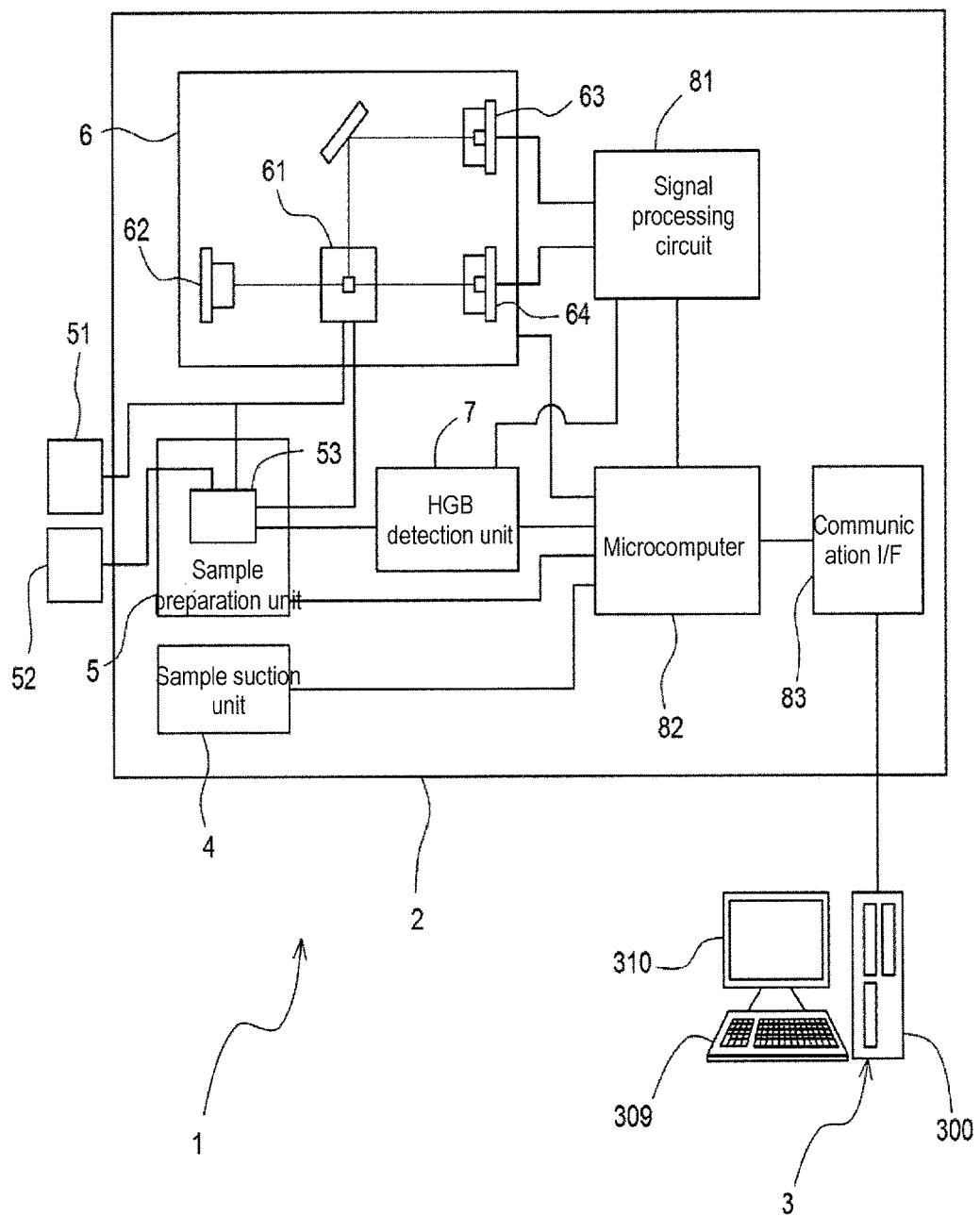
FIG. 1 is a schematic view showing the structure of the blood analyzer of the first embodiment.

The structure of the blood analyzer is described referring to FIG. 1. The blood analyzer 1 is provided with a measuring unit 2 and an information processing unit 3. The measuring unit 2 receives a blood sample, prepares a measurement sample from the blood sample, and optically measures the measurement sample. The information processing unit 3 processes the measurement data obtained by the measurement performed by the measuring unit 2, and outputs the result of the blood sample analysis.

The measuring unit 2 is provided with a sample suction unit 4, sample preparation unit 5, optical detection unit 6, HGB detection unit 7, signal processing circuit 81, microcomputer 82, and communication interface 83.

The sample suction unit 4 has a suction tube, and suctions the blood sample contained in a test tube via the suction tube.

The sample preparation unit 5 has a reaction tank 53, and is connected to reagent containers 51 and 52. The reagent container 51 contains diluting liquid for diluting blood samples. Reagent container 52 contains hemolytic agent. The blood sample suctioned by the sample suction unit 4 and diluting liquid are mixed in the reaction tank 53 to prepare a first measurement sample. The first measurement sample is used in the measurement of red blood cells. The blood sample suctioned by the sample suction unit 4, diluting liquid, and hemolytic agent are mixed in the reaction tank 53 to prepare a second measurement sample. The second measurement sample is used in the measurement of hemoglobin concentration.

The optical detection unit 6 is used in the measurements of red blood cells and auto-fluorescence by a flow cytometric method. The optical detecting unit 6 is provided with a flow cell 61, light source 62, fluorescence detector 63, and scattered light detector 64. The flow cell 61 is supplied the first measurement sample prepared by the sample preparation unit 5 and diluting liquid from the reagent container 51. The flow cell 61 forms a flow in which the first measurement sample is encapsulated in a sheath liquid of diluting liquid.

The light source 62 is a semiconductor light source, which irradiates the flow cell 61 with blue color laser light having a wavelength of 405 nm.

The sensitivity wavelength range of the fluorescence detector 63 is 400 nm or greater but no more than 1000 nm. The sensitivity wavelength range of the scattered light detector 64 is 400 nm or greater but no more than 1000 nm. Avalanche photodiodes may be used as the fluorescence detector 63 and the scattered light detector 64. The fluorescence detector 63 and the scattered light detector 64 detect the light produced from the first measurement sample when light irradiates the flow of the first measurement sample in the flow cell 61. The fluorescence detector 63 and the scattered light detector 64 output analog signals which represent the intensity of the received light. The analog signals output from the fluorescence detector 63 are referred to as "fluorescent light signals" and the analog signals output from the scattered light detector 64 are referred to as "forward scattered light signals."

The HGB detection unit 7 is used in the measurement of hemoglobin concentration by an SLS-hemoglobin method. The HGB detection unit 7 is supplied the second measurement sample from the sample preparation unit 5. The HGB detection unit 7 irradiates light of a 555 nm wavelength on the second measurement sample contained in the cell, and detects the absorbance by the second measurement sample. The HGB detection unit 7 outputs analog signals which reflect the absorbance.

The signal processing circuit 81 performs signal processing on the analog signals output by the fluorescence detector 63, scattered light detector 64, and HGB detection unit 7. The signal processing circuit 81 extracts the peak pulse value contained in the fluorescent light signal and the forward scattered light signal as a characteristic parameter. Below, the peak value of the fluorescent light signal is referred to as "Fluorescence intensity" and the peak value of the forward scattered light signal is referred to as "forward scattered light intensity". The signal processing circuit 81 converts the intensity of the output signal of the HGB detection unit 7 as the characteristic parameter of hemoglobin concentration.

The microcomputer 82 controls the sample suction unit 4, sample preparation unit 5, light detection unit 6, HGB detection unit 7, signal processing unit 81, and communication interface 83.

The communication interface 83 is connected to the information processing unit 3 through a communication cable. The measuring unit 2 performs data communication with the information processing unit 3 through the communication interface 83. The communication interface 83 sends measurement data including each characteristic parameter to the information processing unit 3 when a blood sample measurement is performed.

Figure 2:
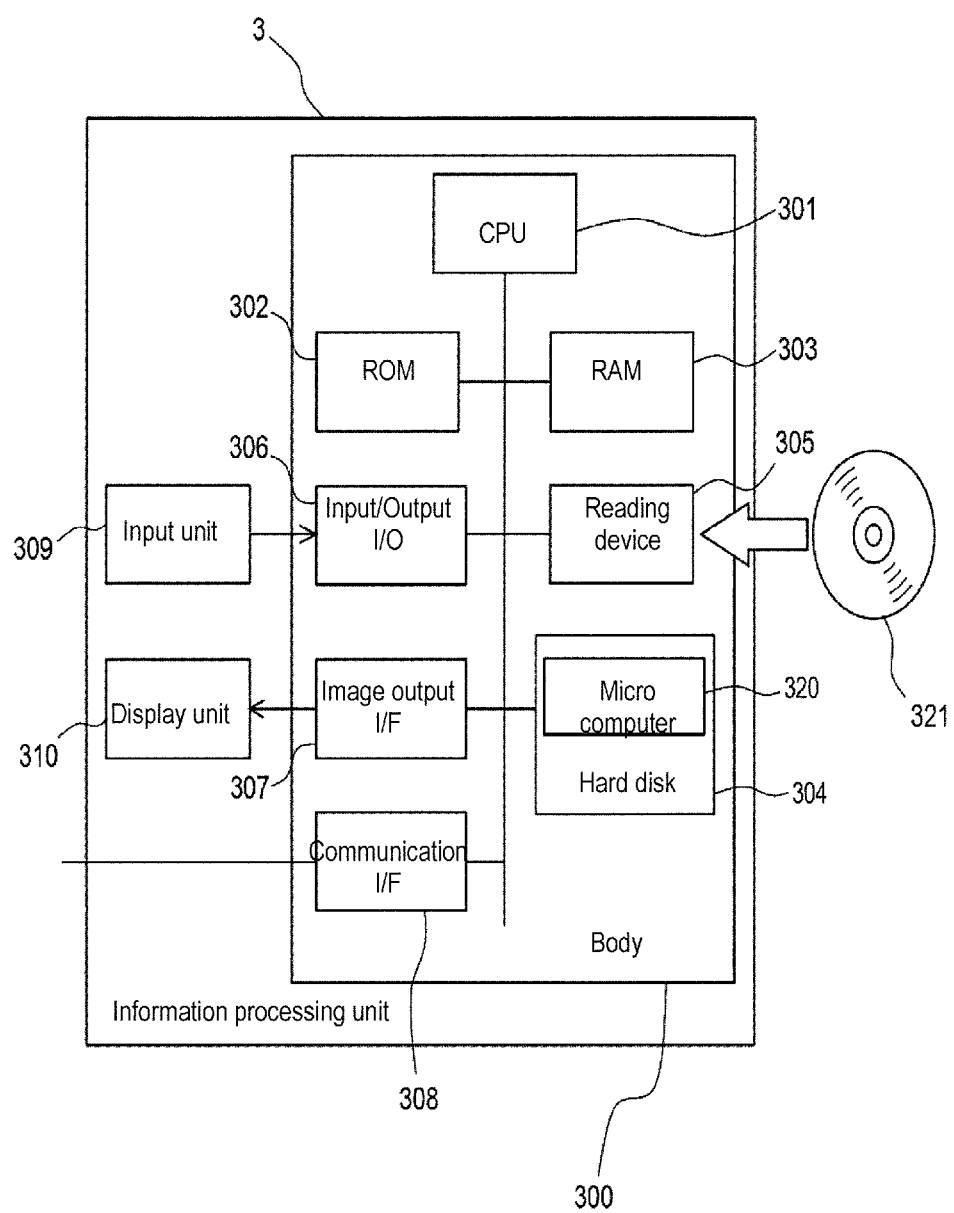
FIG. 2 is a block diagram showing the structure of the information processing unit.

The structure of the information processing unit 3 is described referring to FIG. 2. The information processing unit 3 is configured by a main body 300, input unit 309, and display unit 310. The main body 300 has a CPU (central processing unit) 301, ROM (read only memory) 302, RAM (random access memory) 303, hard disk 304, reading device 305, I/O (Input/Output) interface 306, image output interface 307, and communication interface 308. In the present embodiment, a display which shows images is used as the output unit 310. However, a printer which outputs printing to paper or the like also may be used as the output unit 310.

The CPU 301 executes a computer program stored in the ROM 302 and a computer program loaded in the RAM 303. The RAM 303 is used when reading the computer program recorded on the ROM 302 and on the hard disk 304. The RAM 303 is also used as the work area of the CPU 301 when the CPU 301 executes the computer programs.

A computer program for analyzing measurement data received from the measuring unit 2 and outputting analysis results is installed on the hard disk 304.

The reading device 305 is configured by a floppy disk drive, CD-ROM drive, DVD-ROM drive or the like, and is capable of reading computer programs or data recorded on a portable recording medium 321. A computer program 320 which enables a computer to function as the information processing unit 3 is stored on the portable recording medium 321. The computer program 320 is read from the portable recording medium 321 and installed on the hard disk 304.

The input unit 309 is connected to the I/O interface 306. The output unit 310 is connected to the image output interface 307. The communication interface 308 is connected to the communication interface 83 of the measuring unit 2.

Operation of the Blood Analyzer

Figure 3:
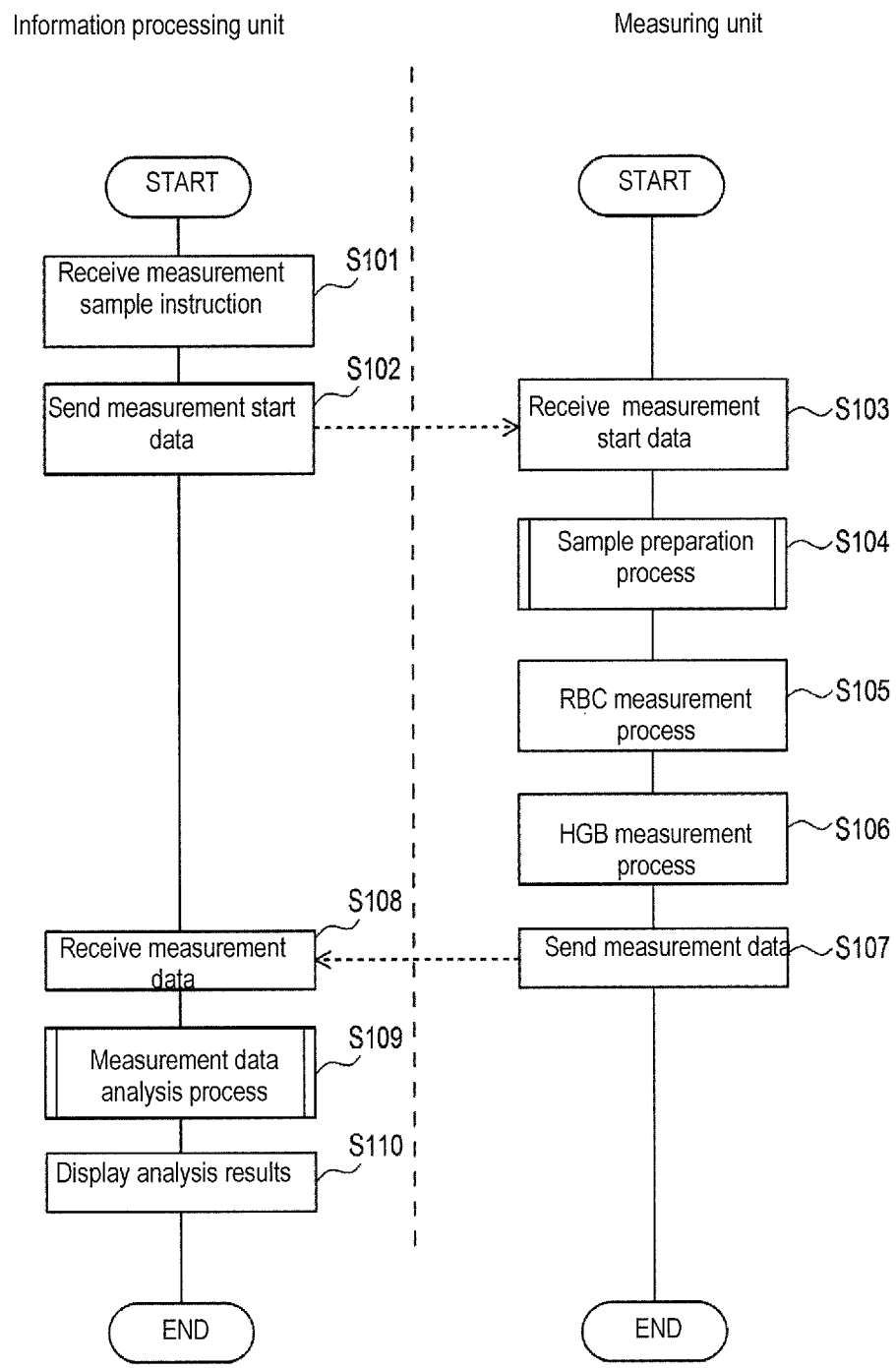
FIG. 3 is a flow chart showing the flow of the operation performed by the blood analyzer of the first embodiment.

The operation of the blood analyzer 1 is described referring to FIG. 3.

In step S101, the CPU 301 of the information processing unit 3 first receives the instruction to execute measurement from the user through the input unit 309. When the instruction to execute measurement is received, the CPU 301 sends instruction data to start the measurement to the measuring unit 2 in step S102. In step S103, the measuring unit 2 receives the instruction data. The microcomputer 82 executes a measurement sample preparation process in step S104, executes an RBC measurement process in step S105, and executes an HGB measurement process in step S106.

Figure 4:
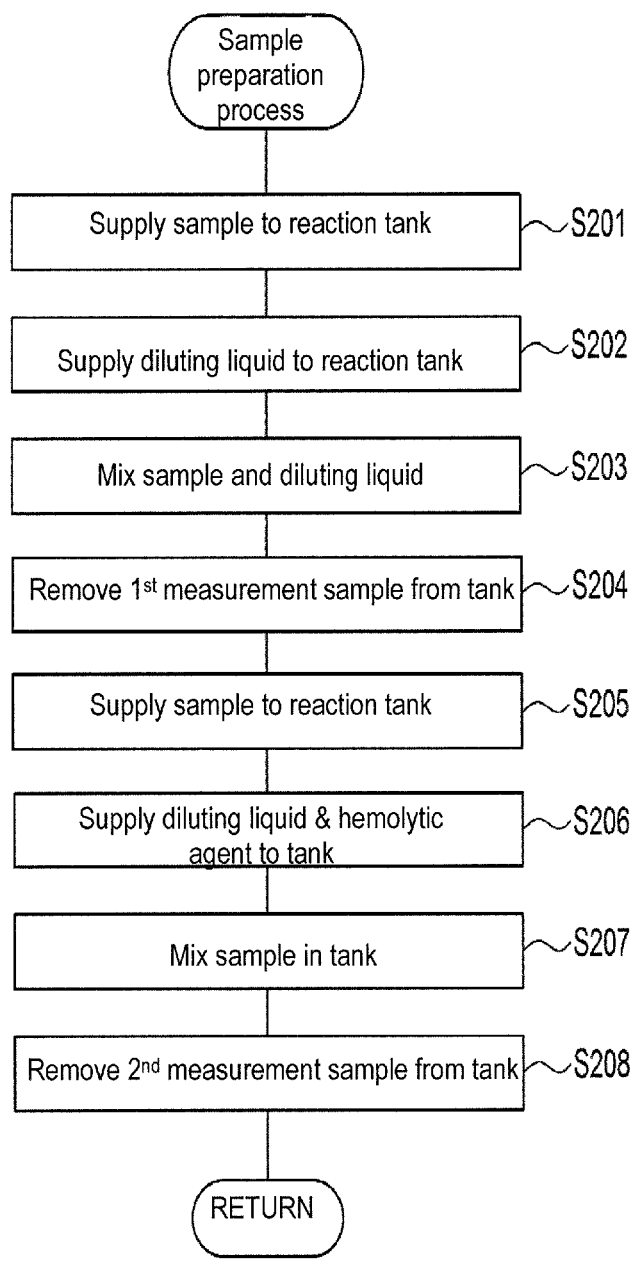
FIG. 4 is a flow chart showing the sequence of the measurement sample preparing process.

The measurement sample preparation process is described referring to FIG. 4. In step S201, the microcomputer 82 controls the sample suction unit 4 to suction a predetermined amount of blood sample from a test tube, and supply the 5 µL of the sample to the reaction tank 53. Then, the microcomputer 82 controls the sample preparation unit 5 and supplies 1020 µL of diluting liquid from the reagent container 51 to the reaction tank 53 in step S202.

The reaction tank 53 is heated to a predetermined temperature by a heater, and the mixture in the reaction tank 53 is mixed in step S203 while in a heated state. The first measurement sample is prepared in the reaction tank 53 through the operations of steps S201 through S203. That is, the sample preparation unit 5 prepares the first measurement sample without hemolysis or staining. In step S204, the first measurement sample is extracted from the reaction tank 53 and supplied to the optical detection unit 6.

In step S205, the microcomputer 82 controls the sample suction unit 4 to supply 3 µL of the sample from the reaction tank 53. In step S206, the microcomputer 82 then controls the sample preparation unit 5 to supply 997 µL of diluting liquid from the reagent container 51 to the reaction tank 53, and supplies 500 µL of hemolytic agent from the reagent container 52 to the reaction tank 53.

In step S207, the mixture in the reaction tank 53 is mixed. The second measurement sample is prepared in the reaction tank 53 through the operations of steps S205 through S207. That is, the sample preparation unit 5 prepares the second measurement sample by performing hemolysis without staining. In step S208, the second measurement sample is extracted from the reaction tank 53 and supplied to the HGB detection unit 7.

When the process of step S208 ends, the microcomputer 82 returns the process to the main routine.

Refer again to FIG. 3. In the RBC measurement process, the first measurement sample is measured by the optical detection unit 6. The first measurement sample together with a sheath fluid is supplies to the flow cell 61. The light source unit 62 irradiates light on the flow of the first measurement sample in the flow cell 61.

When the first measurement sample flows through the flow cell 61, the red blood cells sequentially pass through the flow cell 61. Although there a small amount of protoporphin present in the red blood cells of healthy people, a large amount of protoporphin is present in the red blood cells of patients with iron deficiency anemia. Auto-fluorescence is produced when red blood cells containing a large amount of protoporphin are irradiated by blue-violet laser light. Since auto-fluorescence has a wavelength of 600 nm or greater but no more than 700 nm, the auto-fluorescence produced by each red blood cell can be individually detected by the fluorescence detector 63. On the other hand, auto-fluorescence is virtually absent when red blood cells with a small amount of protoporphin are irradiated by blue laser light. Therefore, auto-fluorescence is not detected due to the low level of light received by the fluorescence detector 63.

Each time the red blood cell is irradiated by light, scattered light is produced from the red blood cell. The scattered light produced from the red blood cell has a wavelength of 450 nm and is detected by the scattered light detector 64.

The fluorescence detector 63 and scattered light detector 64 output electrical signals corresponding to the level of the received light as fluorescent light signals and forward scattered light signals. The signal processing circuit 81 extracts the fluorescence intensity from the fluorescent light signals, and extracts the forward scattered light intensity from the forward scattered light signals.

The RBC measurement process is executed for a predetermined time.

In the HGB measurement process, the second measurement sample is measured by the HGB detection unit 7. The second measurement sample is supplied to the HGB detection unit 7. The HGB detection unit 7 irradiates light at a wavelength of 555 nm on the second measurement sample in the cell, detects the absorbance, and outputs analog signals to the signal processing unit 81. The signal processing unit 81 converts the output signal of the HGB detection unit 7 to a hemoglobin concentration.

After the HGB measurement process, the microcomputer 82 sends the measurement data containing each characteristic parameter to the information processing unit 3 in step S107 and the process ends.

When the information processing unit 3 receives the measurement data in step S108, the CPU 301 executes the measurement data analysis process to generate blood sample analysis data and stores the analysis results in the hard disk 304 in step S109.

Figure 5:
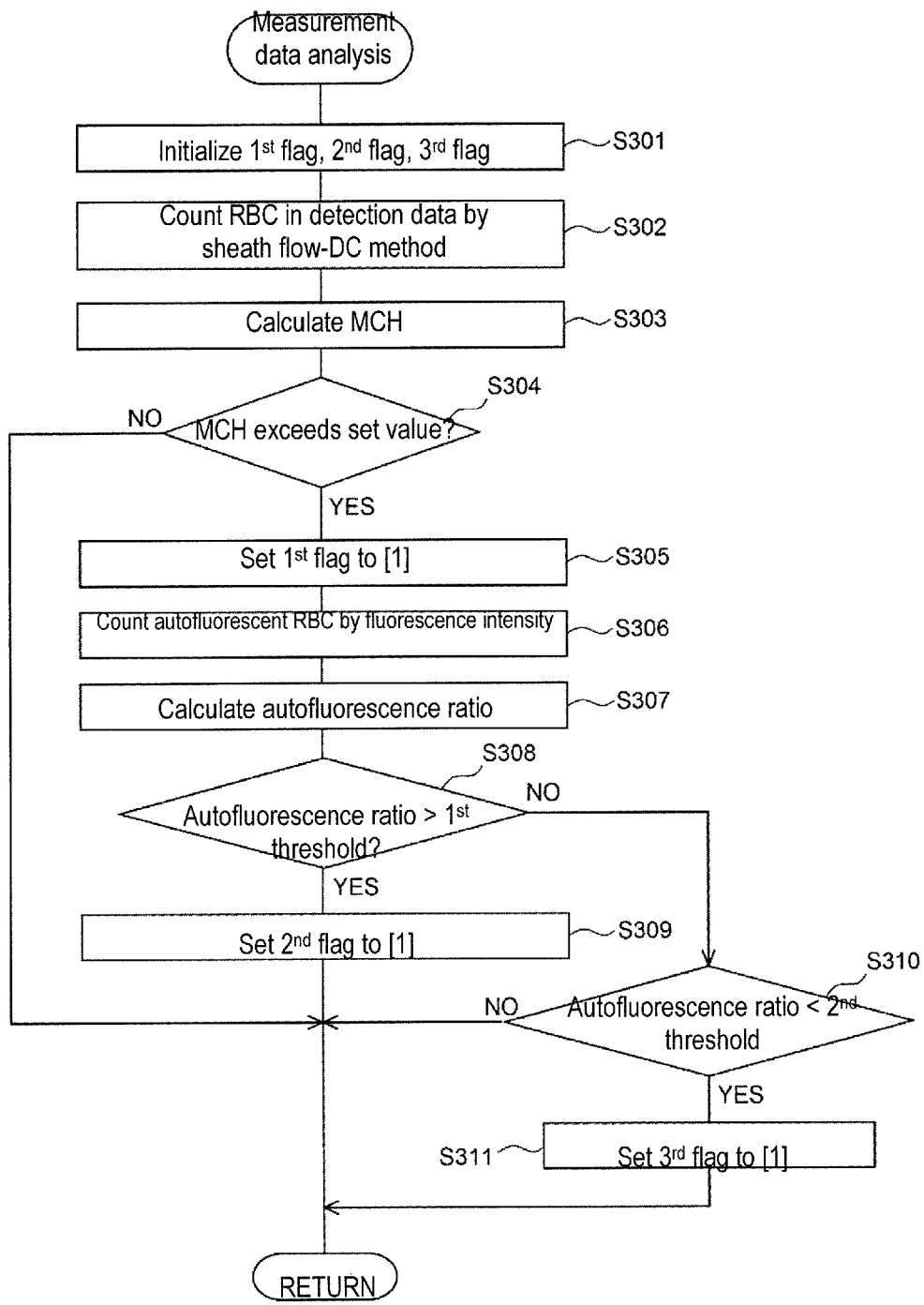
FIG. 5 is a flow chart showing the sequence of the measurement sample analyzing process of the first embodiment.

The measurement data analysis process is described referring to FIG. 5. When the measurement data analysis process starts, the CPU 301 first sets a first flag representing the possibility of microcytic anemia, a second flag representing the possibility of iron deficiency anemia, and a third flag representing the possibility of beta-thalassemia to initial values of zero [0] in step S301. The first flag, second flag, and third flag are established in a specific region of the RAM 303. When the first flag is set at [0], the flag indicates a low possibility of microcytic anemia; when the first flag is set at [1], the flag indicates a high possibility of microcytic anemia. When the second flag is set at [0], the flag indicates a low possibility of iron deficiency anemia; when the second flag is set at [1], the flag indicates a high possibility of iron deficiency anemia. When the third flag is set at [0], the flag indicates a low possibility of beta-thalassemia; when the third flag is set at [1], the flag indicates a high possibility of beta-thalassemia.

The CPU 301 counts the red blood cells in step S302. In the blood analyzer 1, a voltage is applied to the measurement sample flowing through the sheath flow cell, and the red blood cells are detected by a sheath flow-DC detection method which measures the blood cells by capturing the changes in voltage as the blood cells pass through the sheath flow cell. The measurement data include red blood cell detection data. In step S302, the CPU 301 counts the red blood cells based on the red blood cell detection data.

The red blood cells also may be counted using the forward scattered light intensity included in the measurement data instead of the sheath flow-DC method. Red blood cells have a diameter of approximately 7 or 8 μm. The forward scattered light intensity is a characteristic parameter which reflects the size of the blood cell, and the forward scattered light intensity of red blood cells are values within a predetermined range. Accordingly, particles which have a forward scattered light intensity within the predetermined range within which red blood cells occur are designated red blood cells, and also counted as red blood cells. The red blood cells also may be detected using the forward scattered light pulse width, or pulse area instead of the forward scattered light intensity. The red blood cells also may be detected by detecting the side scattered light intensity and using the peak value of the pulse, pulse width, or pulse area of the side scattered light.

The CPU 301 then calculates the mean corpuscular hemoglobin (referred to as "MCH" below) from the red blood cell count and hemoglobin concentration in step S303. MCH is defined by the following equation. Provided that the RGB is the red blood cell count, and HGB is the hemoglobin concentration.

$$MCH(pg) = \frac{HGB(g/dL)}{RBC(\times 10^4/\mu L)} \times 1000 \quad [\text{Eq. 1}]$$

The CPU 301 compares the MCH to a predetermined threshold value and determines the possibility of microcytic anemia in step S304. MCH reflects the amount of hemoglobin in the blood sample. A sample of microcytic anemia has a low MCH value compared to a normal sample. That is, the CPU 301 determines a high possibility of microcytic anemia when the MCH is at or below the threshold value. On the other hand, the CPU 301 determines a low possibility of microcytic anemia when the MCH is greater than the threshold value.

When the MCH is at or below the threshold value, the CPU 301 set the first flag to [1] in step S305. When the MCH is greater than the threshold value, the CPU 301 ends the measurement data analysis process and returns the process to the main routine.

In step S306, the CPU 301 extracts particles for which the fluorescence intensity is greater than a predetermined threshold value from the group of particles designated red blood cells as red blood cells which produce auto-fluorescence (referred to as "auto-fluorescent red blood cells" below), and counts the auto-fluorescent red blood cells. That is, the CPU 301 identifies the individual auto-fluorescence red blood cells by the detected intensity of the auto-fluorescence, and counts the auto-fluorescent red blood cells. The number of auto-fluorescent red blood cells is referred to as "the auto-fluorescent red blood cell count" below. The value of the auto-fluorescence produced by the red blood cells of a patient with iron deficiency anemia is detected as a high value compared to the auto-fluorescence produced by the red blood cells of a person who does not have iron deficiency anemia. In the present embodiment, the auto-fluorescence produced by red blood cells of a person who does not have iron deficiency anemia cannot be detected because it is hidden by noise. In the present embodiment, red blood cells having detected auto-fluorescence above the threshold value are designated as auto-fluorescent red blood cells, and red blood cells having no detected auto-fluorescence above the threshold value are defined as non-auto-fluorescent red blood cells.

In step S307, the CPU 301 calculates the ratio of the number of auto-fluorescent red blood cells relative to the number of red blood cells (referred to as "auto-fluorescence ratio" below) as auto-fluorescence information, and in step S308 compares the auto-fluorescence ratio to a first predetermined threshold value, then determines the possibility of iron deficiency anemia. The auto-fluorescence ratio is information obtained by individually detecting the fluorescence produced by each red blood cell.

Figure 6A:
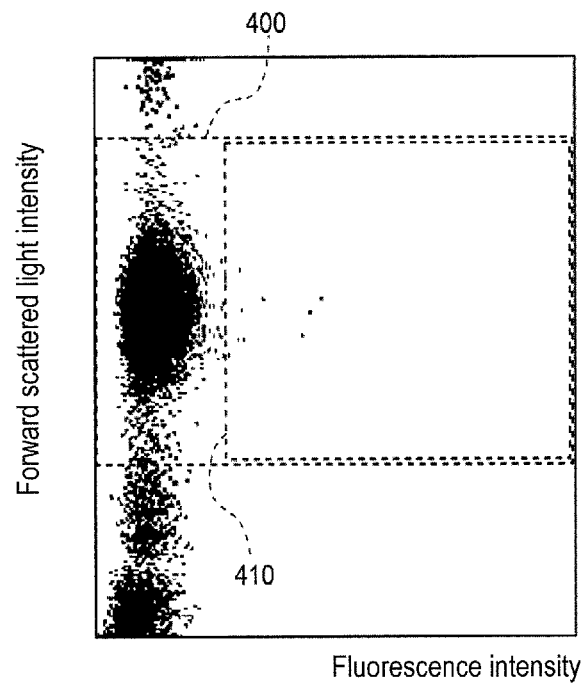
FIG. 6A is a scattergram showing the measurement results of a normal sample.
Figure 6B:
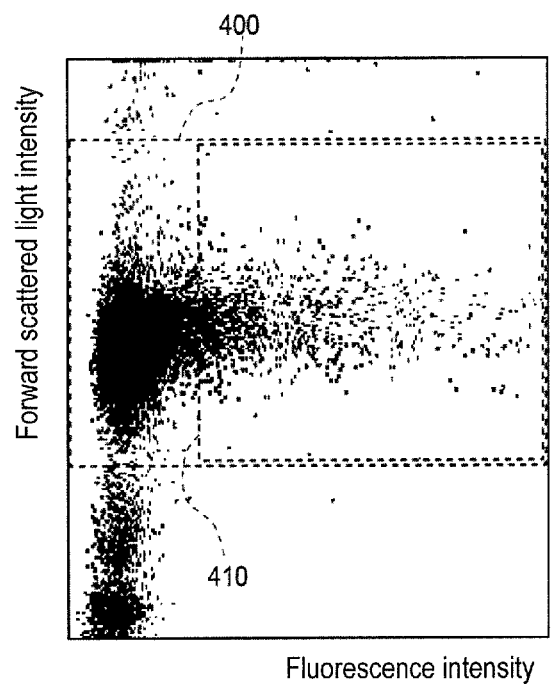
FIG. 6B is a scattergram showing the measurement results of a blood sample collected from a patient with iron deficiency anemia.

In FIG. 6A through 6D, the vertical axis represents the forward scattered light intensity, and the horizontal axis represents the fluorescent light intensity. In FIG. 6A through 6D, the particles appearing in region 400 are designated red blood cells, and the particles appearing in region 410 are designated auto-fluorescent red blood cells. In measurement results of a normal sample, that is, measurement results of blood samples collected from healthy persons, most of the particles do not appear in region 410, as shown in FIG. 6A. That is, particles designated as auto-fluorescent red blood cells are hardly detected. On the other hand, in measurement results of blood samples collected from patients with iron deficiency anemia (referred to as "iron deficiency anemia blood samples" below), many of the particles appear in region 410, as shown in FIG. 6B. That is, a large number of particles designated as auto-fluorescent red blood cells appear.

Figure 6C:
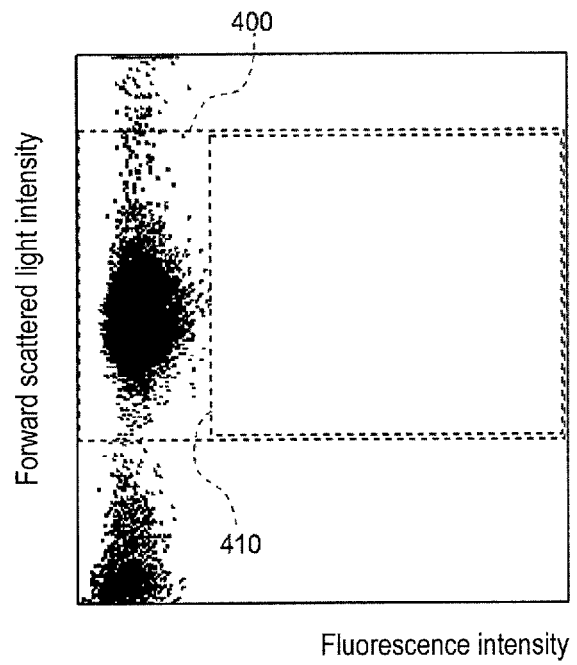
FIG. 6C is a scattergram showing the measurement results of a blood sample collected from a patient with α-thalassemia.
Figure 6D:
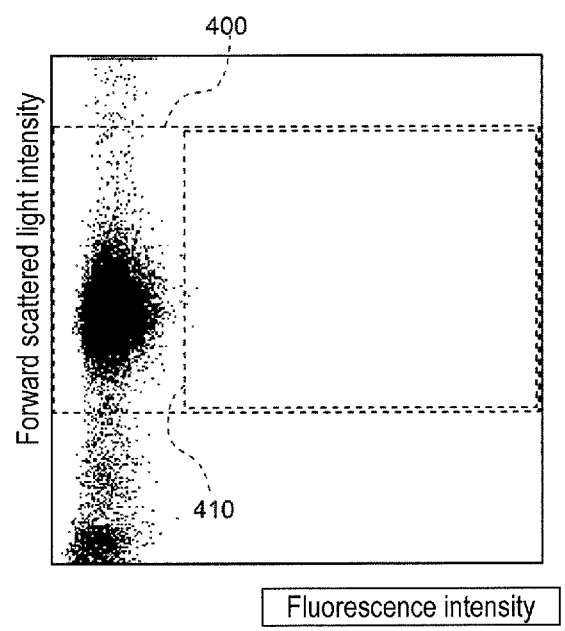
FIG. 6D is a scattergram showing the measurement results of a blood sample collected from a patient with β-thalassemia.

Thalassemia is classified as microcytic anemia similar to iron deficiency anemia, and since the examination values of symptoms and CBC items are similar to those of iron deficiency anemia, it is clinically important to differentiate thalassemia when determining the possibility of iron deficiency anemia. In the measurement results of blood samples collected from patients with thalassemia (referred to as "thalassemia sample" below), particles hardly appear in region 410, as shown in FIGS. 6C and 6D. That is, particles designated as auto-fluorescent red blood cells are hardly detected.

Figure 7:
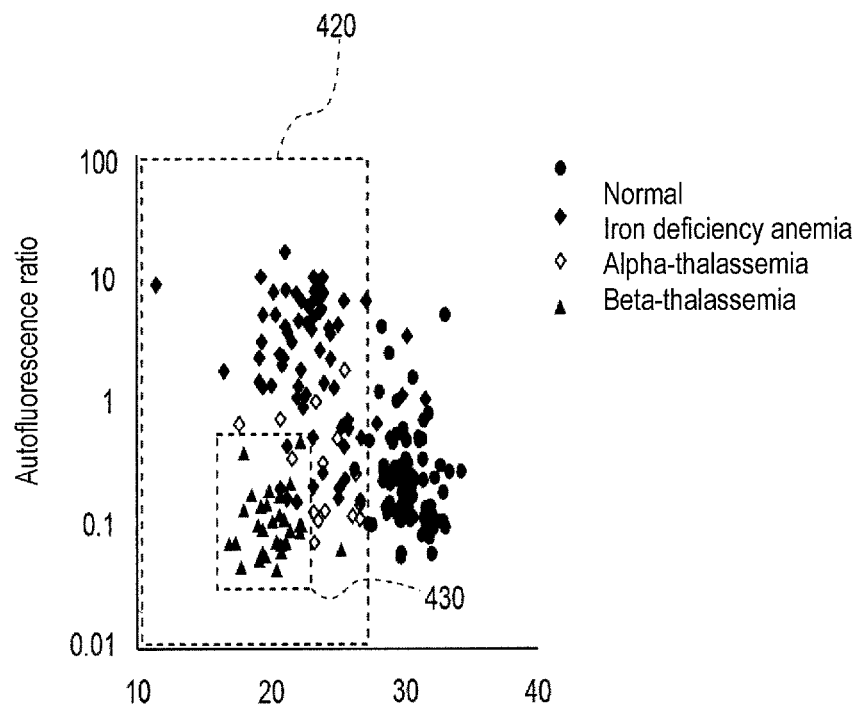
FIG. 7 shows the relationship of the ratios of the number of red blood cells which produce auto-fluorescence relative to the total number of red blood cells, and the MCH in the blood sample.

Refer to FIG. 7. In FIG. 7, the vertical axis represents the auto-fluorescence ratio and the horizontal axis represents MCH. Each point in FIG. 7 represents a blood sample.

Region 420 in FIG. 7 is the range of high possibility of microcytic anemia. Most iron deficiency anemia blood samples and thalassemia blood samples appear in region 420. Among the blood samples in region 420, the iron deficiency anemia blood sample have a higher auto-fluorescence ratio than the thalassemia blood samples, and most microcytic anemia blood samples which have an auto-fluorescence ratio equal to or greater than 1% are iron deficiency anemia blood samples. Most normal samples have an auto-fluorescence ratio less than 1%. From the above it is understood that iron deficiency anemia can be differentiated from thalassemia and normal samples by using the value of the auto-fluorescence ratio or the number of auto-fluorescent red blood cells.

Figure 8:
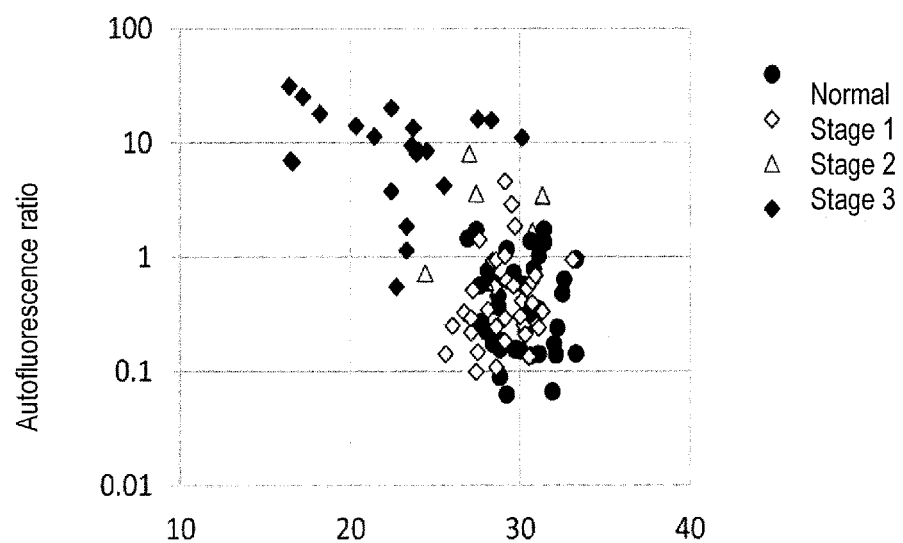
FIG. 8 shows the relationship of the ratios of the number of red blood cells which produce auto-fluorescence relative to the total number of red blood cells, and the MCH at each stage of iron deficiency anemia.

Refer to FIG. 8. In FIG. 8, the vertical axis represents the auto-fluorescence ratio and the horizontal axis represents MCH. Each point in FIG. 8 represents a blood sample. In FIG. 8, normal samples and samples of iron deficiency anemia from stage 1 through stage 3 are shown by changing the type of point. The stages of iron deficiency anemia are described here. Stage 1 is slight iron deficiency anemia. When the examination values in Ferritin among biochemical examination data are lower than the normal range, and the examination values of CRP, ZnPP, sTfR, TIS among biochemical examination items and MCH and hemoglobin concentration among blood count items are within the normal range corresponds to stage 1. Stage 2 is moderate iron deficiency anemia. When the examination values in Ferritin are lower than normal values, examination values in CRP are within the normal range, examination values in ZnPP and sTfR are higher than the normal range, examination value of TfS is lower than the normal range, and examination values in MCH and hemoglobin concentration are within the normal range corresponds to stage 2. Stage 3 is severe iron deficiency anemia. When the examination values in Ferritin are lower than normal values, examination values in CRP are within the normal range, examination values in ZnPP and sTfR are higher than the normal range, examination value of TIS is lower than the normal range, and any examination values in CBC including MCH and hemoglobin concentration are outside the normal range corresponds to stage 3.

In FIG. 8, the normal samples have an auto-fluorescence ratio of 0.1% or higher but no more than 1%, and MCH is mostly distributed within the range of 25 or higher but no more than 35. Stage 1 samples are distributed in approximately the same range as the normal samples. Stage 2 samples have an auto-fluorescence ratio of 1% or higher but no more than 10%, and MCH is mostly distributed within the range of 22 or higher but no more than 32. Stage 3 samples have an auto-fluorescence ratio of 3% or higher but no more than 100%, and MCH is mostly distributed within the range of 15 or higher but no more than 30. From FIG. 8, at least stage 3 iron deficiency anemia samples can be differentiated from normal samples if the first threshold value is set from 3% or higher but no more than approximately 10%.

Refer again to FIG. 7. Among the thalassemia samples, the beta-thalssemia samples have a particularly small auto-fluorescence ratio. Accordingly, among samples which have a high possibility of microcytic anemia, the samples with a small auto-fluorescence ratio can be determined to have a high possibility of beta-thalssemia.

Refer again to FIG. 5. When the auto-fluorescence ratio is equal to or greater than the first threshold value, the CPU 301 sets the second flag to [1] in step S309, ends the measurement data analysis process, and returns the process to the main routine. When the auto-fluorescence ratio is less than the first threshold value, the CPU 301 compares the auto-fluorescence ratio with a predetermined second threshold value and determines the possibility of beta-thalassemia in step S310. The second threshold value is smaller than the first threshold value. When the auto-fluorescence ratio is less than the second threshold value, the CPU 301 sets the third flag to [1] in step S311, ends the measurement data analysis process, and returns the process to the main routine. When the auto-fluorescence ratio is equal to or greater than the second threshold value, the CPU 301 ends the measurement data analysis process and returns the process to the main routine.

When the auto-fluorescence ratio is less than the second threshold value, it is also possible to determine a high possibility of thalassemia including alpha-thalssemia and beta-thalassemia. When the auto-fluorescence ratio is less than the first threshold value, it also is possible to determine a high possibility of thalassemia without using the second threshold value. In a two-dimensional coordinate space in which one coordinate axis is designated for the auto-fluorescence ratio and the other coordinate axis is designated for MCH, the determination area 430 of beta-thalassemia is stipulated as shown in FIG. 7, and is possible to determine a high possibility of beta-thalassemia when the auto-fluorescence ratio and MCH enter the determination area 430.

A configuration also may use the auto-fluorescence ratio to determine iron deficiency anemia without performing a determination related to thalassemia. A configuration also may use the auto-fluorescence ratio to determine thalassemia without performing a determination related to iron deficiency anemia.

In the measurement data analysis process, white blood cell count (WBC), platelet count (PLT), hematocrit value (HCT), mean corpuscular volume (MCV), mean corpuscular hemoglobin concentration (MCHC), neutrophil count (NEUT), lymphocyte count (LYMPH), eosinophil count (EU), monocyte count (MONO), reticulocyte count (RET) and the like are determined.

Refer again to FIG. 3. In step S110, the CPU 301 displays the analysis results on the output unit 310, and the process ends. The analysis results include red blood cell count, hemoglobin concentration, MCH, auto-fluorescent red blood cell count, and auto-fluorescence ratio of each measurement result, and reference information for diagnosis. When the first flag is set at [1], the reference information includes information indicating the high possibility of microcytic anemia. When the second flag is set at [1], the reference information includes information indicating the high possibility of iron deficiency anemia. When the third flag is set at [1], the reference information includes information indicating the high possibility of beta-thalassemia.

Figure 9:
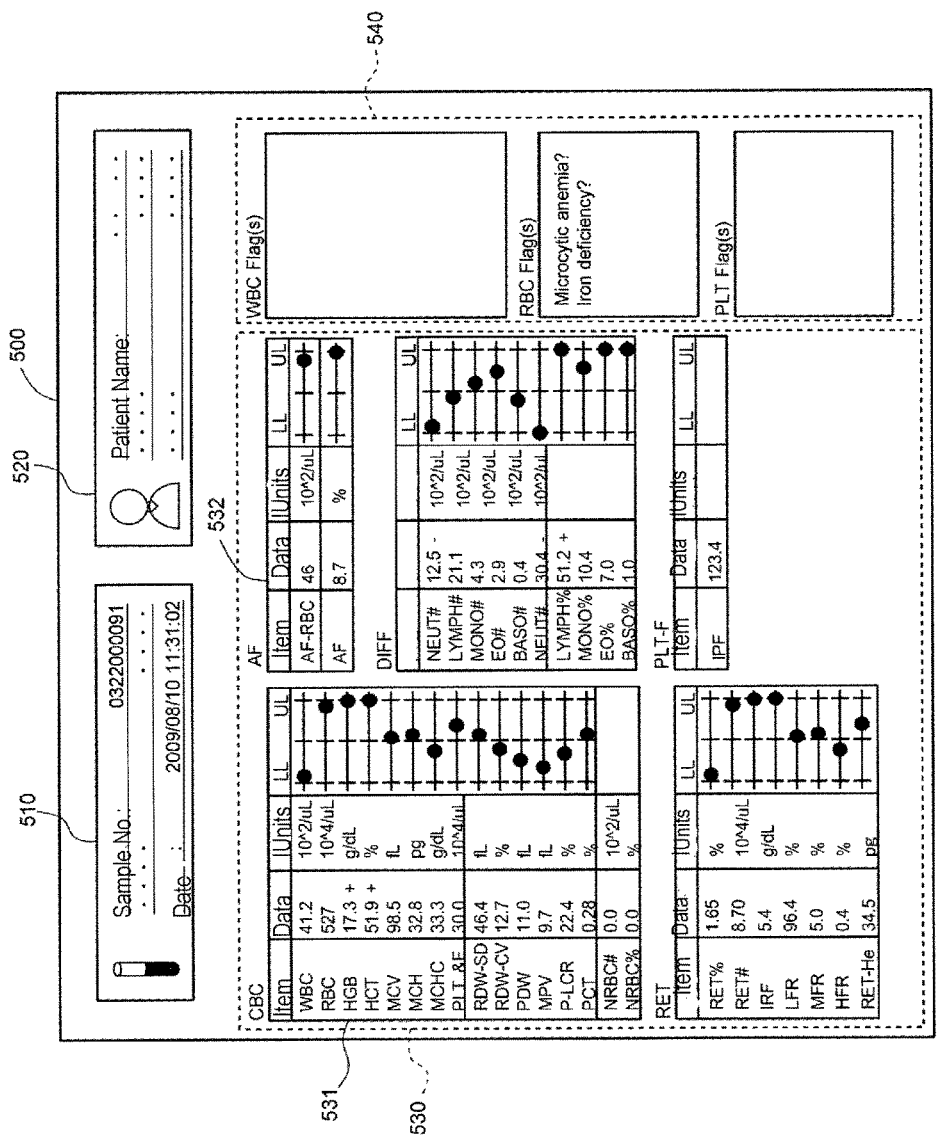
FIG. 9 shows a display example of analysis results in the first embodiment.

The displayed analysis results are described below referring to FIG. 9. An analysis results screen 500 is displayed on the output unit 310. The analysis results screen 500 has a sample information display region 510, patient information display region 520, measurement results display region 530, and reference information display region 540. The measurement results display region 530 has a CBC item display region 531, and auto-fluorescent item display region 532.

The sample information display region 510 displays sample information based on the analysis results shown on the analysis results screen 500. Information of the patient from whom the sample was collected is displayed in the patient information display region 520.

Measurement values of each item obtained by the measurement data analysis process are displayed in the measurement results display region 530. Measurement values of basic measurement items in blood cell analysis are displayed in the CBC item display region 531. The measurement values displayed in the CBC item display region 531 include red blood cell (RBC), hemoglobin concentration (HGB), and MCH measurement values. Measurement values of measurement items related to auto-fluorescence are displayed in the auto-fluorescence item display region 532. The measurement values displayed in the auto-fluorescence item display region 532 include auto-fluorescent red blood cell count (AF-RBC), and auto-fluorescence ratio (AF).

Reference information is displayed for the user in the reference information display region 540 when obtained results should be reported to the user for consideration of sample abnormality through the measurement data analysis process. In the measurement data analysis process, when the first flag is set to [1], the message [Microcytic anemia?] information indicating a high possibility of microcytic anemia is displayed in the reference information display region 540. In the measurement data analysis process, when the second flag is set to [1], the message [Iron deficiency anemia?] information indicating a high possibility of iron deficiency anemia is displayed in the reference information display region 540. In the measurement data analysis process, when the third flag is set to [1], the message [Beta-thalassemia?] information indicating a high possibility of beta-thalassemia is displayed in the reference information display region 540.

The following effects are obtained by the blood analyzer 1 configured as described above. When blue laser light irradiates the red blood cells, auto-fluorescence is detected from the red blood cells which have large protoporphin content, and auto-fluorescence is not detected from red blood cells which have slight protoporphin content. Auto-fluorescence is detected from red blood cells of iron deficiency anemia samples with almost no detection of auto-fluorescence from red blood cells of normal samples and thalassemia samples. Accordingly, it is possible to determine a high possibility of iron deficiency anemia rather than thalassemia by detecting auto-fluorescence. When a high possibility of iron deficiency anemia has been determined, information indicating a high possibility of iron deficiency anemia is output. Information indicating a high possibility of iron deficiency anemia is information which is clinically useful and is therefore provided to the user.

Among samples which have a high possibility of microcytic anemia, samples with almost no detected auto-fluorescence from red blood cells have a high possibility of beta-thalassemia. A high possibility of beta-thalassemia can be determined therefore using the auto-fluorescence ratio. When a high possibility of beta-thalassemia has been determined, information indicating a high possibility of beta-thalassemia is output. Information indicating a high possibility of beta-thalassemia is information which is clinically useful and is therefore provided to the user.

The blood analyzer 1 performs a determination regarding microcytic anemia, and not only iron deficiency anemia and beta-thalassemia. The blood analyzer 1 can provide the user with information aiding diagnosis of very mild anemia by outputting determination results related to microcytic anemia, and determination results related to iron deficiency anemia or beta-thalassemia.

Evaluation Testing

The present inventors prepared an evaluation apparatus of identical configuration as the blood analyzer of the first embodiment, and performed evaluation tests. In the evaluation tests, 71 normal samples, 67 iron deficiency anemia samples, 26 alpha-thalassemia samples, and 30 beta-thalassemia samples were measured using the evaluation apparatus, and iron deficiency anemia and thalassemia were differentiated. For comparison, the above samples were subjected to Green & King, England & Fraser, and Mentzer differentiation methods, and iron deficiency anemia and thalassemia were differentiated. Please reference Patent Document 1 regarding these differentiation methods.

The differentiation results of the evaluation apparatus and the differentiation results of the other differentiation methods were subjected to ROC analysis. The results of ROC analysis are shown in the table below.

TABLE 1

| Differentiation method | AUC |
| --- | --- |
| Evaluation device | 0.950 |
| Green & King | 0.892 |
| England & Fraser | 0.874 |
| Mentzer | 0.841 |

AUC (area under the curve indicates a high differentiation performance approaching 1. From the ROC analysis it can be understood that excellent differentiation results were obtained by the evaluation apparatus compared to the generally advocated differentiation methods Second Embodiment In the second embodiment, a blood analyzer configured to monitor the status of iron deficiency anemia of a patient is described.

Blood Analyzer Structure

The structure of the blood analyzer of the second embodiment is identical to the structure of the blood analyzer of the first embodiment, like structural elements are denoted by like reference numbers, and the description is omitted.

Operation of the Blood Analyzer

The operation of the blood analyzer of the second embodiment is identical to the operation of the blood analyzer of the first embodiment with the exception of the measurement data analysis process and display of the analysis results. In the second embodiment, the measurement data analysis process and the display of the analysis results are described and descriptions of other operations are omitted.

Figure 10:
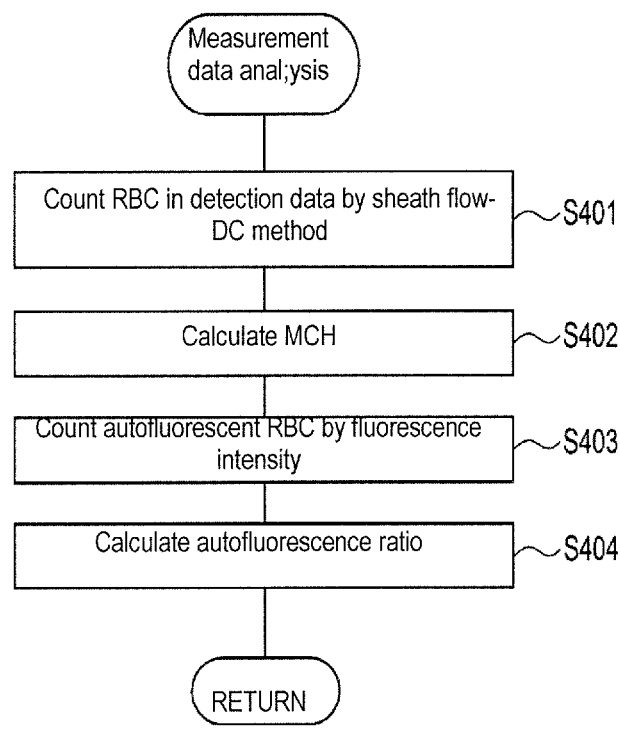
FIG. 10 is a flow chart showing the sequence of the measurement data analyzing process of a second embodiment.

Refer to FIG. 10. When the measurement data analysis process is started, the CPU 301 first counts the red blood cells in step S401 using the red blood cell detection data obtained by the sheath flow-DC method.

The CPU 301 then calculates the MCH from the red blood cell count and hemoglobin concentration in step S402.

In step S403, the CPU 301 extracts particles for which the auto-fluorescence intensity is equal to or greater than a predetermined threshold value from among the particle group designated red blood cells as auto-fluorescent red blood cells, and counts the auto-fluorescent red blood cells.

The CPU 301 calculates the auto-fluorescence ratio in step S404. When the process of step S404 ends, the CPU 301 ends the measurement data analysis process, and returns the process to the main routine.

Figure 11:
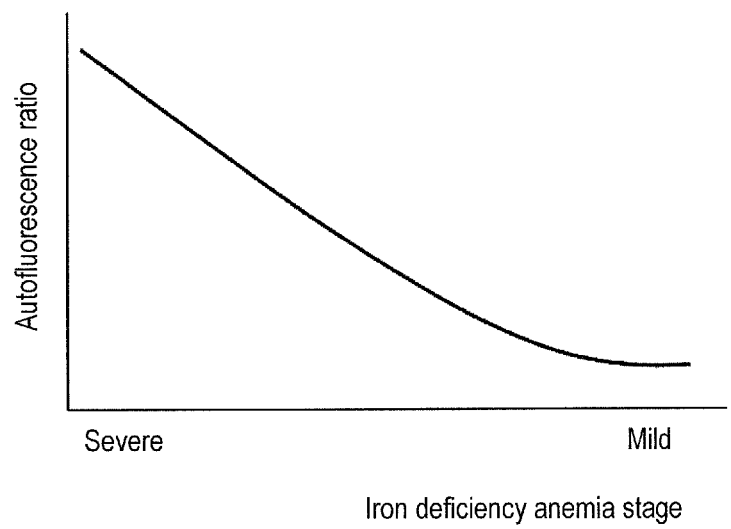
FIG. 11 is a graph showing the relationship of the ratios of the number of red blood cells which produce auto-fluorescence relative to the total number of red blood cells, and the stage of iron deficiency anemia.

The value of the auto-fluorescence ratio is described referring to FIG. 11. In FIG. 11, the horizontal axis represents the stage of iron deficiency anemia and the vertical axis represents the auto-fluorescence ratio. The auto-fluorescence ratio increases as the degree of iron deficiency anemia becomes more severe, and the auto-fluorescence ratio decreases as the degree of iron deficiency anemia moderates.

Accordingly, the degree of iron deficiency anemia can be estimated by the value of the auto-fluorescence ratio.

Figure 12:
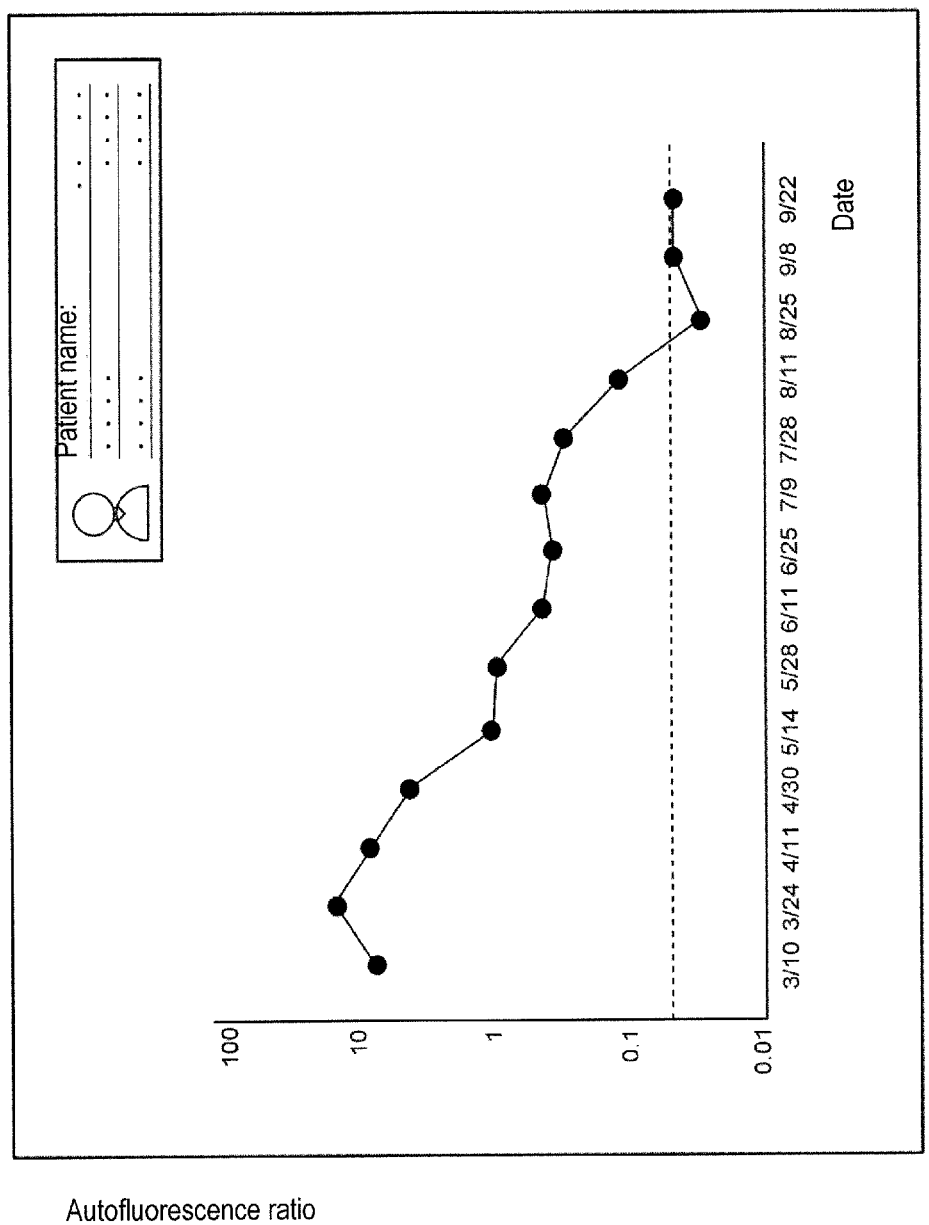
FIG. 12 shows a display example of analysis results in the second embodiment.

The analysis results obtained by the measurement data analysis process are displayed on the output unit 310. The displayed analysis results are described below referring to FIG. 12. The CPU 301 displays a time series graph of the auto-fluorescence ratio measured on several days for the same patient as analysis results. In FIG. 12, the horizontal axis represents the date and the vertical axis represents the auto-fluorescence ratio. Analysis results for a patient receiving treatment for iron deficiency anemia are shown in FIG. 12.

In the example of FIG. 12, the auto-fluorescence ratio decreases over time. The dashed line in FIG. 12 is baseline of determination related to iron deficiency anemia. The user can determine a high possibility of iron deficiency anemia when the auto-fluorescence ratio is above the baseline, and determine a low possibility of iron deficiency anemia when the auto-fluorescence ratio is below the baseline. In the example shown in FIG. 12, the auto-fluorescence ratio decreases over time from a position above the baseline, and ultimately the auto-fluorescence ratio is positioned near the baseline indicating the iron deficiency anemia is improving.

In the blood analyzer of the second embodiment, the user can monitor the status of the iron deficiency anemia by continuously collecting blood samples from the same patient and measuring the respective blood samples via the configuration described above.

A single blood analyzer can perform not only the monitoring function of the status of iron deficiency anemia using a flow cytometric method, but also perform the function of making a determination regarding anemia using the flow cytometric method as described in the first embodiment.

Third Embodiment

In the third embodiment, the described blood analyzer enlarges and images a smear sample of blood smeared on a glass slide via a microscope, and detects blood cells based on the image of the blood cells.

Blood Analyzer Structure

Figure 13:
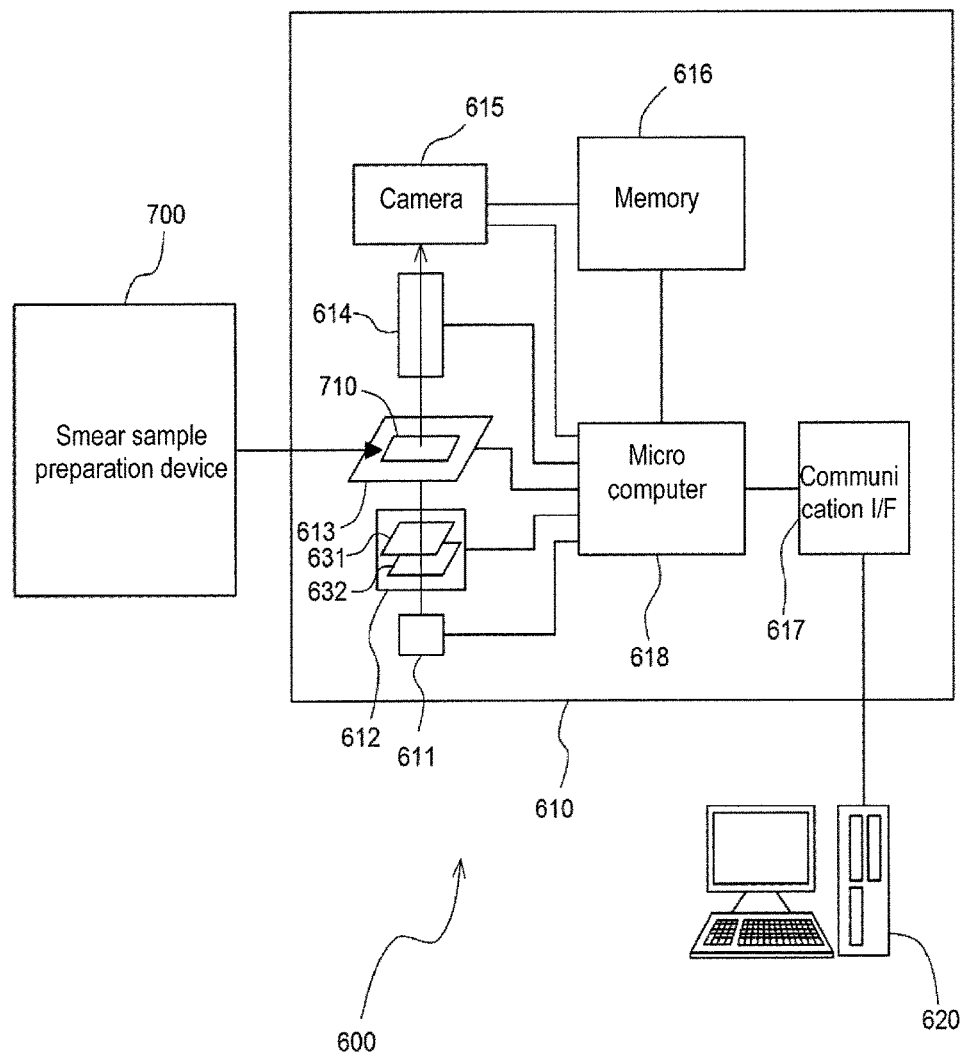
FIG. 13 is a schematic view showing the structure of the blood analyzer of a third embodiment.

The structure of the blood analyzer is described referring to FIG. 13. The blood analyzer 600 is provided with a measuring unit 610 and an information processing unit 620. The measuring unit 610 is capable of imaging blood cells in a smear sample, and the information processing unit 620 is capable of processing the obtained image and detecting blood cells. A smear sample preparing device 700 is connected to the measuring unit 610.

The smear sample preparing device 700 suctions a blood sample from a test tube, dilutes the blood sample to prepare a measurement sample, titrates the measurement sample onto a glass slide, and thinly spreads the measurement sample to prepare a smear sample 710. The smear sample preparing device 700 supplies the prepared smear sample 710 to the measuring unit 610.

The measuring unit 610 is provided with a light source part 611, filter part 612, stage 613, lens part 614, camera 615 which is a fluorescent light detector, memory 616, communication interface 617, and microcomputer 618.

The light source part 611 is capable of irradiating multi-wavelength light such as white light. The filter part 612 has a plurality of narrow band filters. The narrow band filters include a first filter 631 with a central wavelength of 405 nm, and a second filter 632 with a central wavelength of 640 nm. The filter part 612 selects the first filter 631 and the second filter 632. The selected narrow band filter transmits the light emitted from the light source part 611.

The stage 613 supports the smear sample 710 transported from the smear sample preparing device 700. The light transmitted by the narrow band filter irradiates the smear sample 710 supported on the stage 613.

The lens part 614 enlarges the image of the smear sample 710. The camera 615 receives the transmission light of the smear sample 710 through the lens part 614, and produces a color image. The memory 616 records the image produced by the camera 615.

The communication interface 617 is connected to the information processing unit 620 through a communication cable. The communication interface 617 is capable of sending the image recorded in the memory 616 to the information processing unit 620.

The microcomputer 618 controls the light source part 611, filter part 612, stage 613, lens part 614, camera 615, memory 616, and communication interface 617.

The information processing unit 620 is a computer, and is configured by a CPU, ROM, RAM, hard disk, input unit, display unit, and communication interface. A computer program configured to process the image produced by the camera 615 is installed on the hard disk.

Operation of the Blood Analyzer

The smear sample preparing device 700 prepares a smear sample 710 and supplies the smear sample 710 to the measuring unit 2. In the measuring unit 2, the stage 613 supports the smear sample 710. The light source part 611 irradiates light toward the smear sample 710, the filter part 612 selects the first filter 631, and subsequently selects the second filter 632. When the light emitted from the light source part 611 passes through the first filter 631, the smear sample 710 is irradiated by blue light. When the light emitted from the light source part 611 passes through the second filter 632, the smear sample 710 is irradiated by red light.

A light source part which irradiates light having a central wavelength of 405 nm and a light source part which irradiates light having a central wavelength of 640 nm also may be provided so as to irradiate light on the smear sample 710 by switching the light source rather than the configuration of switching the filter which transmits multi-wavelength light.

The camera 615 produces an image both when the smear sample 710 is irradiated with blue light and when the smear sample 710 is irradiated with red light. Below, the image produced when blue light is irradiated is referred to as the first image, and the image produced when red light is irradiated is referred to as the second image. The first image and the second image are recorded in the memory 616 and sent to the information processing unit 620.

Figure 14:
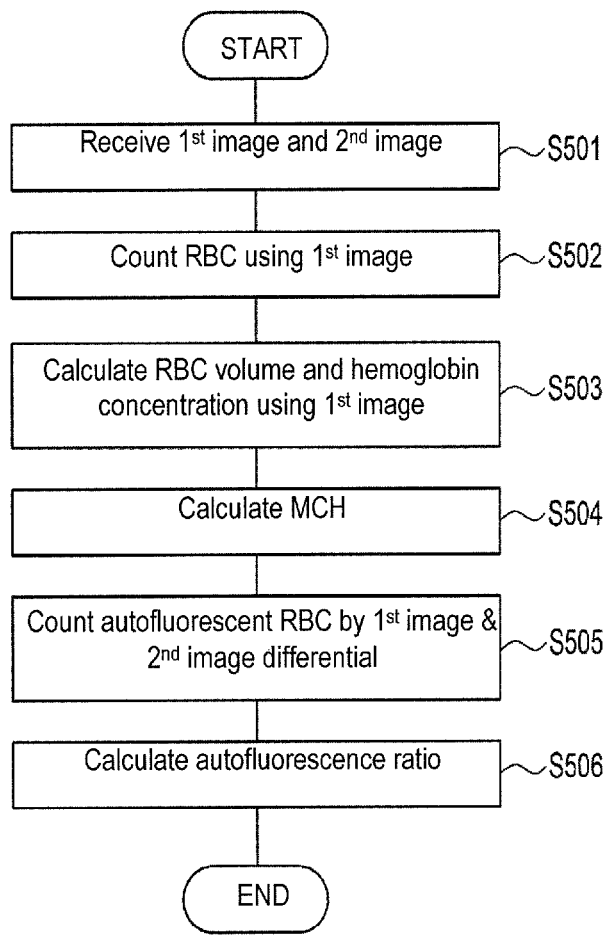
FIG. 14 is a flow chart showing the flow of the operation performed by the information processing unit of the third embodiment.

The operation of the information processing unit 620 is described referring to FIG. 14. The information processing unit 620 receives the first image and the second image in step S501. The CPU of the information processing unit 620 detects the red blood cells using the first image and counts the number of red blood cells in step S502. Red blood cells absorb blue light and white blood cells scarcely absorb blue light. Accordingly, red blood cells and white blood cells can be differentiated and detected using the first image.

The CPU calculates the red blood cell volume and calculates the hemoglobin concentration using the first image in step S503. The red blood cell volume is determined form the number of pixels in the area recognized as a red blood cell. The hemoglobin concentration is determined from the density of each pixel in the area recognized as a red blood cell, and the red blood cell volume.

The CPU calculates MCH in step S504. The equation described in the first embodiment is used in calculating MCH.

In step S505, the CPU detects the number of auto-fluorescent red blood cells, and counts the auto-fluorescent red blood cells. In step S505, the differential of the first image and the second image is acquired, and the auto-fluorescent red blood cells are detected based on this differential.

In step S506, the CPU determines the auto-fluorescence ratio, and the process ends.

The information processing unit 620 makes a determination regarding microcytic anemia based on MCH, makes a determination regarding iron deficiency anemia and a determination regarding thalassemia based on the auto-fluorescence ratio identically to the information processing unit 3 of the blood analyzer 1 of the first embodiment. The measurement results of red blood cell count, hemoglobin concentration, MCH, auto-fluorescent red blood cell count, auto-fluorescence ratio, determination results regarding microcytic anemia, and determination results regarding iron deficiency anemia and thalassemia are output to the display unit for the information processing unit 620.

The status of iron deficiency anemia can be monitored by displaying the auto-fluorescence ratio values in time series identically with the second embodiment by detecting the auto-fluorescent red blood cells based on the image of the blood cells without making a determination regarding microcytic anemia and without performing any of the determination regarding iron deficiency anemia, determination regarding thalassemia, and determination regarding microcytic anemia. A single blood analyzer also may perform the function of monitoring the status of iron deficiency anemia, and the function of making a determination regarding anemia using the images of the blood cells.

In the blood analyzer 600 of the third embodiment described above, a determination regarding anemia can be made by using a captured image of blood cells. If the image of the detected auto-fluorescent red blood cells is output together with information related to iron deficiency anemia, diagnosis is more effectively supported since it becomes even easier to diagnose iron deficiency anemia.

Fourth Embodiment

A blood analyzer configured to detect auto-fluorescence from reticulocytes contained in a blood sample, and making a determination related to iron deficiency anemia and thalassemia is described. Matured red blood cells are referred to as "red blood cells" below and are differentiated from reticulocytes.

Blood Analyzer Structure

Figure 15:
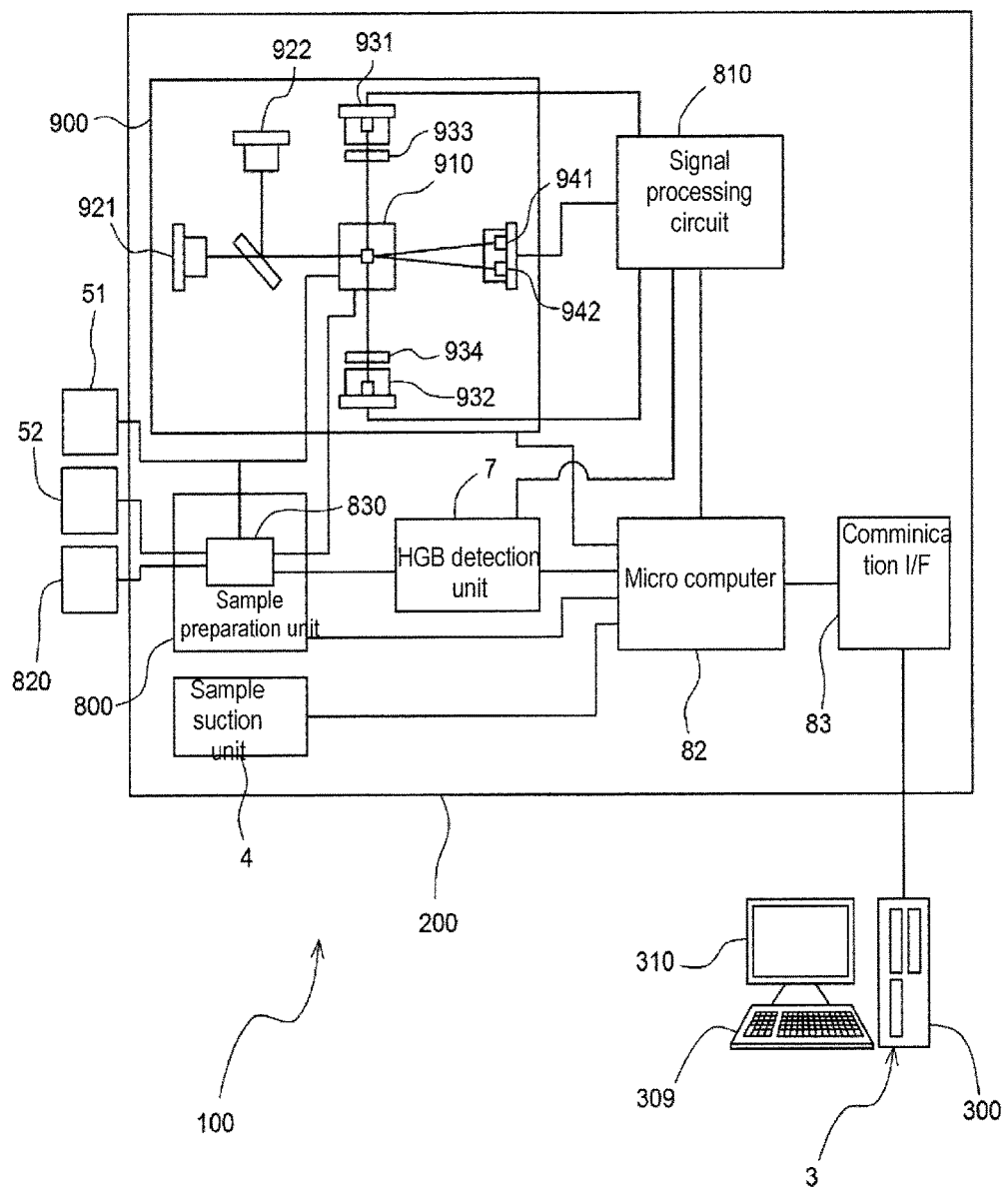
FIG. 15 is a schematic view showing the structure of the blood analyzer of a fourth embodiment.

The structure of the blood analyzer 100 is described referring to FIG. 15. The structure is identical to the structure of the blood analyzer 1 of the first embodiment, identical reference numbers are affixed, and the description is omitted.

The measuring unit 200 has a sample preparation unit 800. The sample preparation unit 800 has a reaction tank 830, and is connected to reagent containers 51, 52, and 820. The reagent container 820 contains staining reagent for specifically staining reticulocytes. For example, reagent disclosed in U.S. Pat. No. 3,425,830, or Fluorocel RET, a product of Sysmex Corporation may be used as the staining reagent.

The blood sample suctioned by the sample suction unit 4 and diluting liquid are mixed in the reaction tank 830 to prepare a first measurement sample. The first measurement sample is used in the measurement of red blood cells. The blood sample suctioned by the sample suction unit 4, diluting liquid, and hemolytic agent are mixed in the reaction tank 830 to prepare a second measurement sample. The second measurement sample is used in the measurement of hemoglobin concentration. The blood sample suctioned by the sample suction unit 4, diluting liquid, and staining reagent are mixed in the reaction tank 830 to prepare a third measurement sample. The third measurement sample is used in the measurement of reticulocytes.

The optical detection unit 900 is used in the measurements of red blood cells, reticulocytes, and auto-fluorescence by a flow cytometric method. The optical detection unit 900 is provided with a flow cell 910, first light source part 921, second light source part 922, first fluorescence detecting part 931, second fluorescence detecting part 932, first scattered light detecting part 941, and second scattered light detecting part 942. The structure of the flow cell 910 is identical to the structure of the flow cell 61 of the first embodiment, and description is therefore omitted.

The first light source part 921 and the second light source part 922 are semiconductor laser light sources, respectively. The first light source part 921 irradiates the flow cell 910 with red laser light having a wavelength of 640 nm. The second light source part 922 irradiates the flow cell 910 with blue laser light having a wavelength of 405 nm. The first light source part 921 and the second light source part 922 irradiate light at two vertically separated positions of the flow cell 910.

The sensitivity wavelength range of the first fluorescence detecting part 931 is 400 nm or greater but no more than 1000 nm. An avalanche photodiode may be used as the first fluorescence detecting part 931. A first filter 933 is disposed in front of the first fluorescence detecting part 931. The first filter 933 blocks light between a wavelength of 610 nm and greater but no more than 650 nm, and transmits light at a wavelength of 660 nm and greater.

The sensitivity wavelength range of the second fluorescence detecting part 932 is 400 nm or greater but no more than 1000 nm. An avalanche photodiode may be used as the second fluorescence detecting part 932. A second filter 934 is disposed in front of the second fluorescence detecting part 932. The second filter 934 transmits light at wavelengths of 420 nm through 630 nm, and 650 nm and greater. Accordingly, the second filter 934 blocks laser light at 405 nm and 640 nm.

The respective sensitivity wavelength range of the first scattered light detecting part 941 and the second scattered light detecting part 942 are 400 nm and greater but no more than 1000 nm. Photodiodes may be used as the first scattered light detecting part 941 and the second scattered light detecting part 942. The first scattered light detecting part 941 and the second scattered light detecting part 942 are respectively disposed at two vertically separated locations.

When the first light source part 921 irradiates red laser light, that is the first light, on the blood cells in the flow cell 910, scattered light (referred to as "first forward scattered light" below) is produced, and the first forward scattered light is received by the first scattered light detecting part 941. The second scattered light detecting part 942 does not receive the first forward scattered light produced by the red laser light because it is disposed at a different position from the first scattered light detecting part 941. When the second light source part 922 irradiates blue laser light, that is the second light, on the blood cells in the flow cell 910, scattered light (referred to as "second forward scattered light" below)

is produced, and the second forward scattered light is received by the second scattered light detecting part 942. The first scattered light detecting part 941 does not receive the second forward scattered light produced by the blue laser light because it is disposed at a different position from the second scattered light detecting part 942.

When the first light source part 921 irradiates the first light, red laser light, in the flow cell 910, fluorescent light of the first wavelength of 660 nm or greater is produced when the reticulocytes stained by staining reagent from the reagent container 820 pass through the flow cell 910. The first filter 933 transmits the fluorescent light of the first wavelength, and the transmitted light is received by the first fluorescence detecting part 931. The first light is irradiated in a different direction from the second light, and no image is formed in the second fluorescence detecting part 932. Accordingly, the second fluorescence detecting part 932 does not receive the fluorescence of the first wavelength.

When the second light source part 922 irradiates the second light, blue laser light, in the flow cell 910, auto-fluorescence is produced at the second wavelength near 630 nm when the red blood cells or reticulocytes pass through the flow cell 910. The second filter 934 transmits the auto-fluorescence and the auto-fluorescence is received by the second fluorescence detecting part 932. The first fluorescence detecting part 931 does not receive the auto-fluorescence.

The first fluorescence detecting part 931, second fluorescence detecting part 932, first scattered light detecting part 941, and second scattered light detecting part 942 respectively output analog signals representing the intensity of the received light. Below, the analog signals output from the first fluorescence detecting part 931 are referred to as "first fluorescence signals", the analog signals output from the second fluorescence detecting part 932 are referred to as "second fluorescence signals", the analog signals output from the first scattered light detecting part 941 are referred to as "first forward scattered light signals", and the analog signals output from the second scattered light detecting part 942 are referred to as "second forward scattered light signals".

The signal processing circuit 810 performs signal processing on the analog signals respectively output by the first fluorescence detecting part 931, second fluorescence detecting part 932, first scattered light detecting part 941, and second scattered light detecting part 942. The signal processing circuit 810 extracts the peak pulse value contained in the first fluorescence signal, second fluorescence signal, first forward scattered light signal, and the second forward scattered light signal as a characteristic parameter. Below, the peak value of the first fluorescence signal is referred to as "first fluorescence intensity", the peak value of the second fluorescence signal is referred to as "second fluorescence intensity", the peak value of the first forward scattered light signal is referred to as "first forward scattered light intensity", and the peak value of the second forward scattered light signal is referred to as "second forward scattered light intensity".

Operation of the Blood Analyzer

Figure 16A:
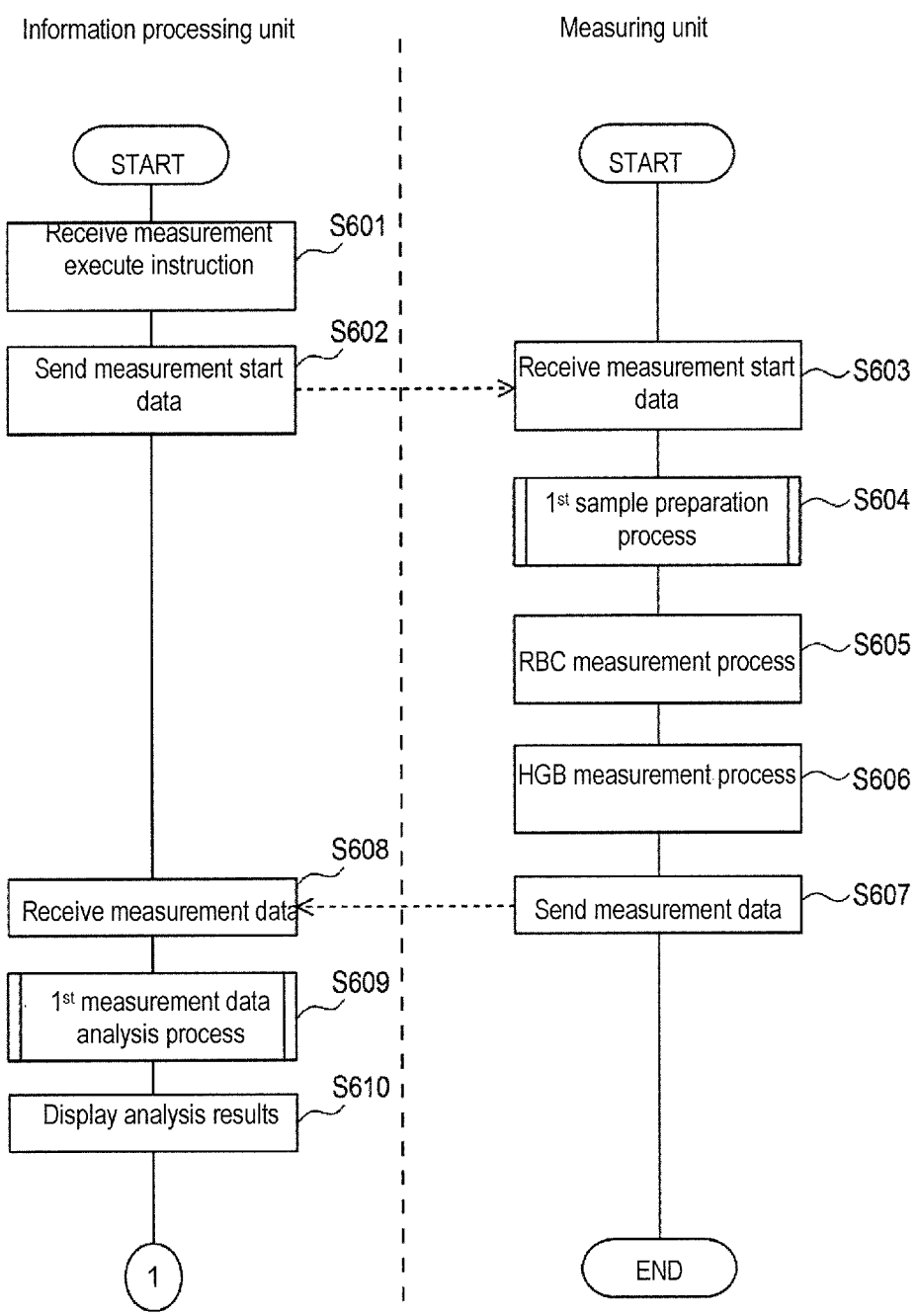
FIG. 16A is a flow chart showing the flow of the operation performed by the blood analyzer of the first embodiment.
Figure 16B:
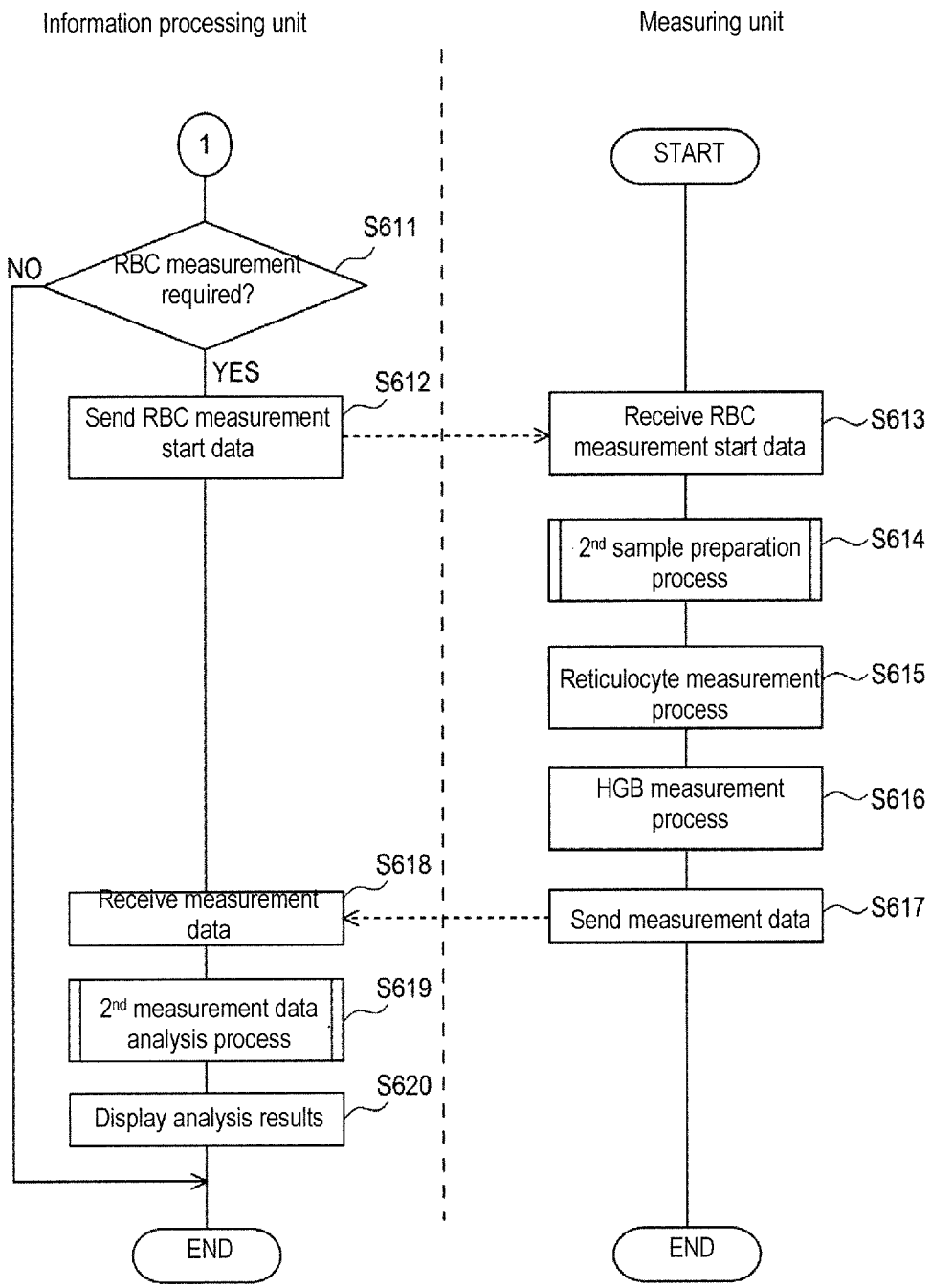
FIG. 16B is a flow chart showing the flow of the operation performed by the blood analyzer of the first embodiment.

The operation of the blood analyzer 100 is described referring to FIGS. 16A and 16B. Since the process in steps S601 through S603 are identical to the process of steps S101 through S103 of the first embodiment, the description is omitted. The first measurement sample preparation process of step S604 is identical to the measurement sample preparation process of step S101 of the first embodiment with the exception of the exclusion of the preparation of the first measurement sample and the second measurement sample in the reaction tank 830, and description is omitted.

In the RBC measurement process of step S605, the first measurement sample is measured by the optical detection unit 900. The first measurement sample together with a sheath fluid is supplied to the flow cell 910. The second light source part 922 irradiates light on the flow of the first measurement sample in the flow cell 910.

When the red blood cells contain protoporphin and the red blood cells are irradiated with blue leaser light, auto-fluorescence is produced. Since auto-fluorescence has a wavelength near 630 nm, the auto-fluorescence emitted by each red blood cell can be individually detected by the second fluorescence detecting part 932. On the other hand, auto-fluorescence is virtually absent when red blood cells with a small amount of protoporphin are irradiated by blue laser light. Therefore, auto-fluorescence is not detected due to the low value of the level of light received by the fluorescence detecting part 932.

Each time the red blood cell is irradiated by light, scattered light is produced from the red blood cell. Since the forward scattered light produced by the red blood cell is the second forward scattered light having a wavelength of 405 nm, the second forward scattered light is detected by the second scattered light detecting part 942.

The first fluorescence detecting part 932 and the second scattered light detecting part 942 output electrical signals corresponding to the level of the received light as second fluorescence signals and second forward scattered light signals. The signal processing circuit 810 extracts the second fluorescence intensity from the second fluorescence signals, and extracts the second forward scattered light intensity from the second forward scattered light signals.

The RBC measurement process is executed for a predetermined time.

Since the process in steps S606 through S610 are identical to the process of steps S106 through S110 of the first embodiment, the description is omitted. However, the second fluorescence intensity is equivalent to the fluorescence intensity in the first embodiment, and the second forward scattered light intensity is equivalent to the forward scatter light intensity in the first embodiment.

The CPU 301 determines whether the measurement of the reticulocytes is necessary in step S611. In step S611, the CPU 301 determines whether the third flag is set at [1], that is, determines whether a high possibility of beta-thalassemia has been determined in the measurement data analysis process. When the third flag is set at [1], the CPU 301 determines that reticulocyte measurement is necessary, the process moves to step S612. When the third flag is set at [0], the CPU 301 determines that reticulocyte measurement is unnecessary, the process ends.

In step S612, the CPU 301 sends instruction data to start the measurement of reticulocytes to the measuring unit 200. In step S613, the measuring unit 200 receives the instruction data. The microcomputer 82 executes the second measurement sample preparation process in step S614, executes the reticulocyte measurement process in step S615, and executes the HGB measurement process in step S616.

Figure 17:
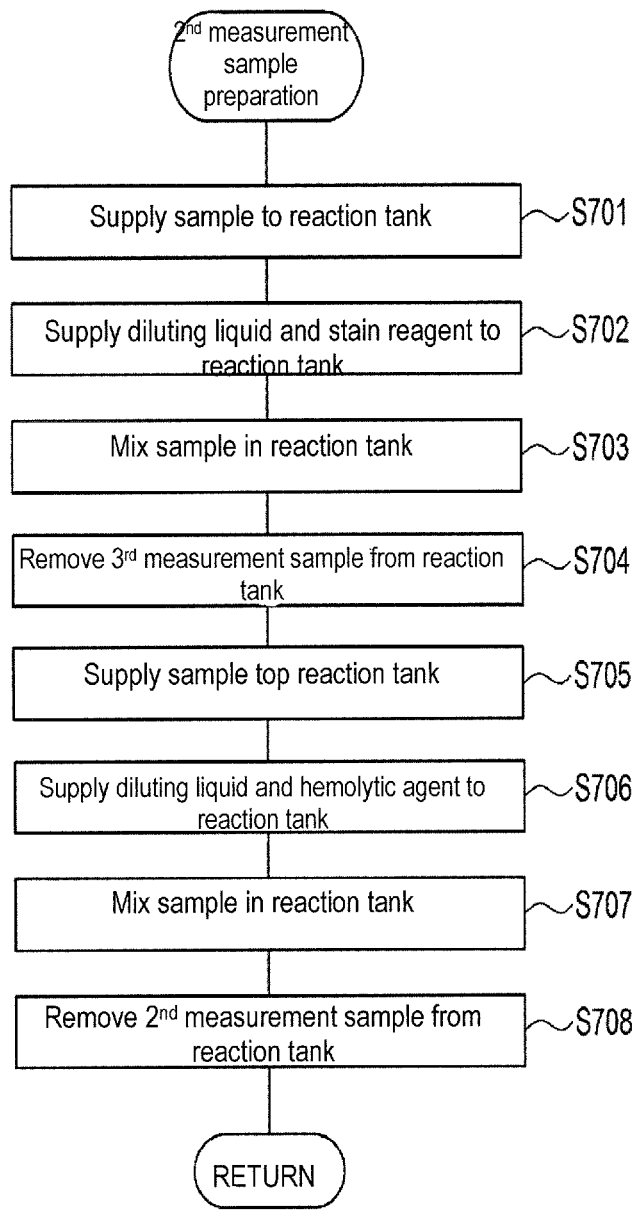
FIG. 17 is a flow chart showing the sequence of a second measurement sample preparing process.

The second measurement sample preparation process is described referring to FIG. 17. In step S701, the microcomputer 82 controls the sample suction unit 4, again suctions a predetermined amount of the blood sample from the test tube from which blood sample was suctioned in step S201, and supplied the predetermined amount of sample to the reaction tank 830. In step S702, the microcomputer 82 controls the sample preparation unit 800 to supply a predetermined amount of diluting liquid from the reagent container 51 and a predetermined amount of staining reagent from the reagent container 820 to the reaction tank 830.

The reaction tank 830 is heated to a predetermined temperature by a heater, and the mixture in the reaction tank 830 is mixed in step S703 while in a heated state. The third measurement sample is prepared in the reaction tank 830 through the operations of steps S701 through S703. The reticulocytes in the third measurement sample are stained by the staining reagent. In step S704, the third measurement sample is extracted from the reaction tank 830 and supplied to the optical detection unit 900.

When the process of step S704 ends, the sample preparation unit 800 prepares the second measurement sample via the process of steps S705 through S708. Since the process in steps S705 through S708 are identical to the process of steps S205 through S208 of the first embodiment, the description is omitted.

When the process of step S708 ends, the microcomputer 82 returns the process to the main routine.

Refer again to FIG. 16B. In the reticulocyte measuring process of step S615, the optical detection unit 900 performs measurements of the third measurement sample. The third measurement sample together with a sheath fluid is supplied to the flow cell 910. The first light source part 921 and the second light source part 922 simultaneously irradiate light on the flow of the third measurement sample in the flow cell 910.

When the red laser light from the first light source part 921 irradiates the reticulocytes passing through the flow cell 910, fluorescence at a first wavelength and red first forward scattered light are produced. The first fluorescence detecting part 931 receives the fluorescence of the first wavelength, and outputs first fluorescence signals. The first scattered light detecting part 941 receives the first forward scattered light, and outputs first forward scattered light signals.

If the reticulocytes and red blood cells passing through the flow cell 910 contain protoporphin, auto-fluorescence of the second wavelength and blue second forward scattered light are produced when the flow cell 910 is irradiated by blue laser light emitted from the second light source part 922. The second fluorescence detecting part 932 receives the auto-fluorescence and outputs a second fluorescence signal. The second scattered light detecting part 942 receives the second forward scattered light, and outputs second forward scattered light signals. If the reticulocytes and red blood cells passing through the flow cell 910 contain scant protoporphin, auto-fluorescence is only slightly produced and the second fluorescence detecting part 932 does not detect the auto-fluorescence even when the flow cell 910 is irradiated by blue laser light emitted from the second light source part 922. The second forward scattered light is produced identically to when reticulocytes and red blood cells contain protoporphin, and the second scattered light detecting part 942 receives the second forward scattered light and outputs a second forward scattered light signal.

Figure 18:
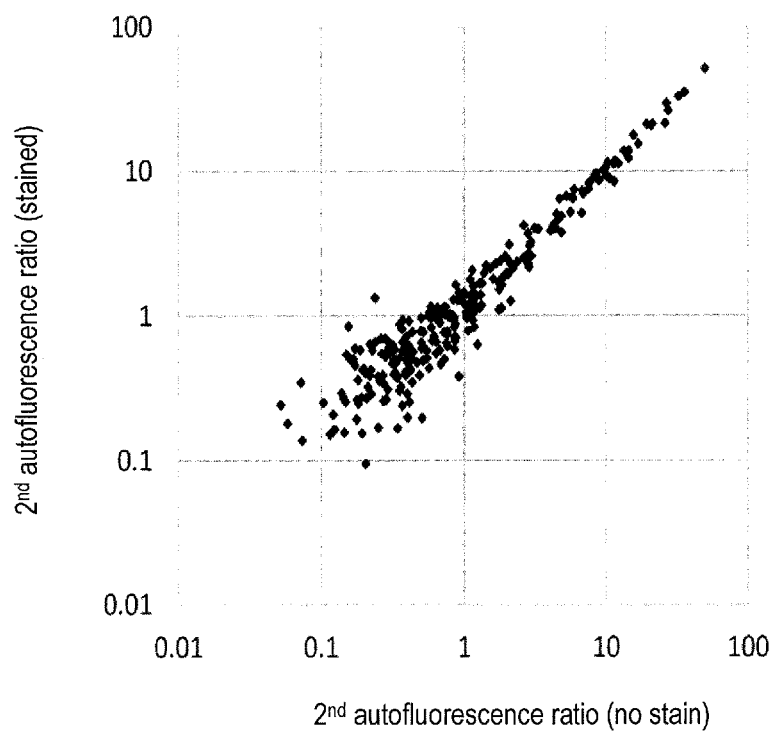
FIG. 18 is a graph which compares the result of the detection of auto-fluorescence produced by stained reticulocytes, and the result of detection of auto-fluorescence produced by unstained reticulocytes.
Figure 20:
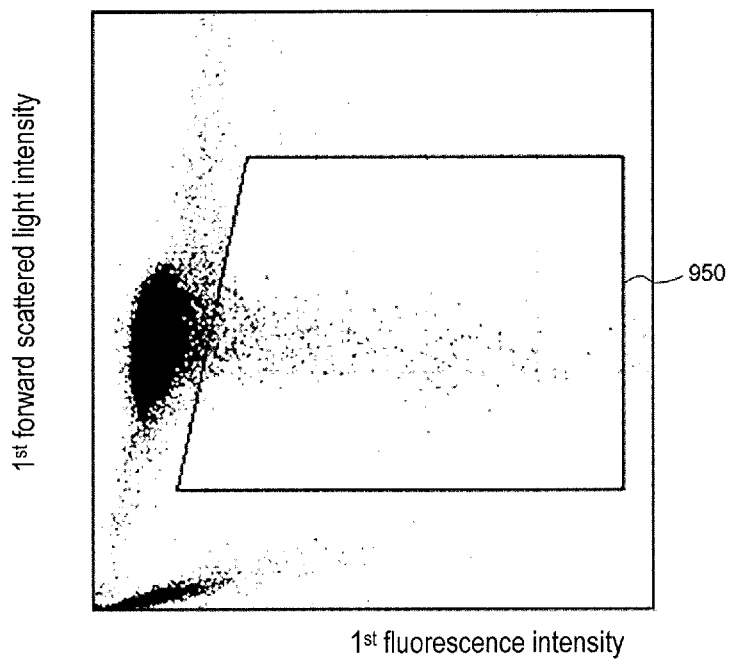
FIG. 20 shows the reticulocyte detection range in a two-dimensional coordinate space of a first fluorescence intensity and a first forward scattered light intensity.

In the reticulocyte measurement process, the auto-fluorescence of reticulocytes stained by staining reagent is detected. In this case there is a problem of not reducing the accuracy of detection of auto-fluorescence by staining reticulocytes. Influences on the detection of auto-fluorescence by staining reticulocytes is described referring to FIG. 18. In FIG. 18, the vertical axis represents the ratio of the number of reticulocytes producing auto-fluorescence relative to the number of reticulocytes (referred to as "second auto-fluorescence ratio" below) obtained by irradiating blue laser light on a sample containing reticulocytes specifically stained by staining reagent, and the horizontal axis represents the second auto-fluorescence ratio obtained by irradiating blue laser light on a sample containing unstained reticulocytes. As shown in FIG. 20, the second auto-fluorescence ratio in the case of stained reticulocytes strongly correlates with the second fluorescence ratio in the case of unstained reticulocytes. Per above, it is understood that the presence of reticulocyte stain has negligible influence on the detection of auto-fluorescence.

Refer again to FIG. 16B. The HGB measurement process of step S616 is identical to the HGB measurement process in the first embodiment.

After the HGB measurement process, the microcomputer 82 sends the measurement data containing each characteristic parameter to the information processing unit 3 in step S617 and the process ends.

When the information processing unit 3 receives the measurement data in step S618, the CPU 301 executes the second measurement data analysis process to generate blood sample analysis data and stores the analysis results in the hard disk 304 in step S619.

Figure 19:
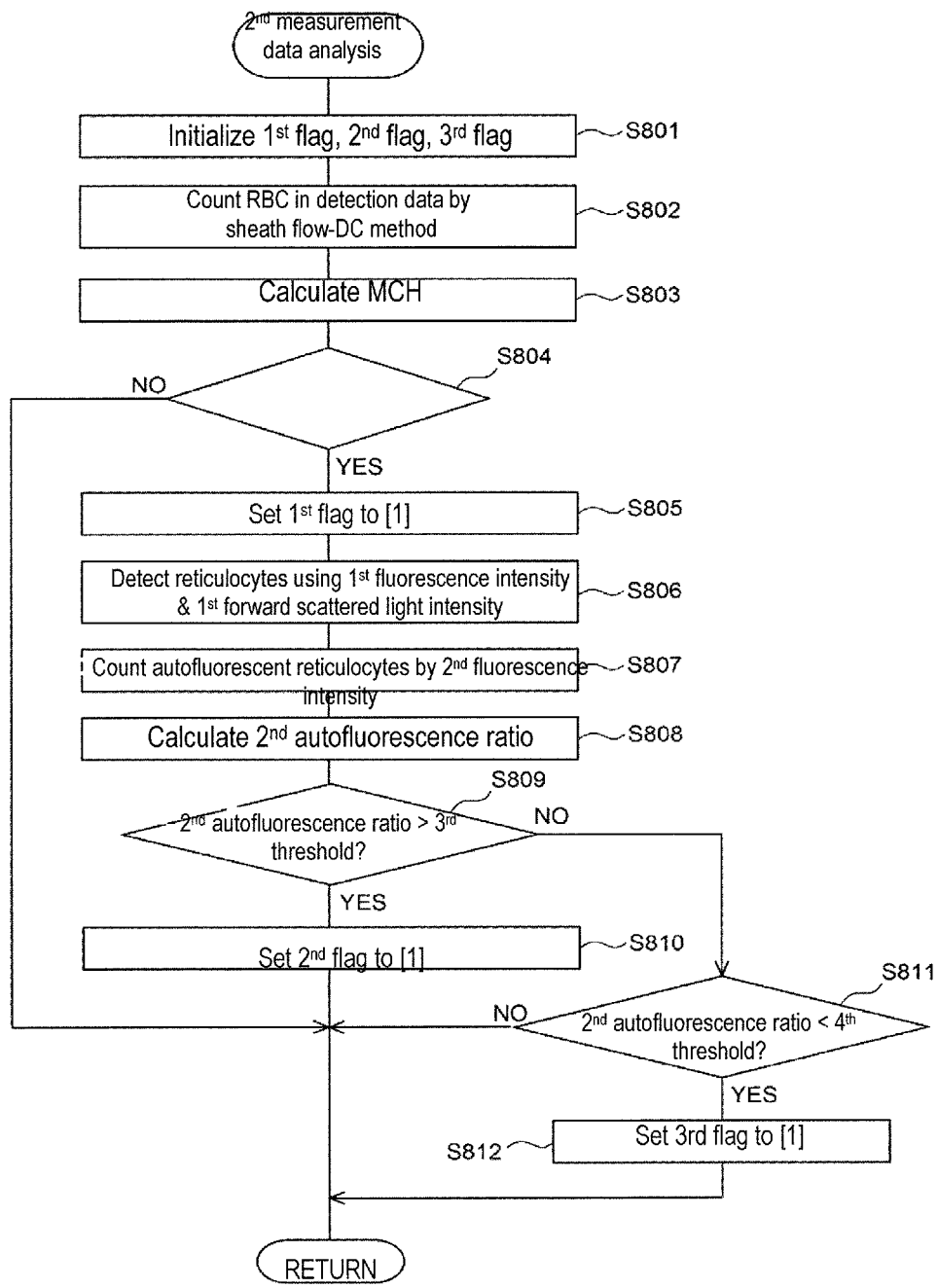
FIG. 19 is a flow chart showing the sequence of the second measurement data analyzing process of the fourth embodiment.

The second measurement data analysis process is described referring to FIG. 19. Since the process in steps S801 through S805 are identical to the process of steps S301 through S305 of the first embodiment, the description is omitted.

In step S806, the CPU 301 detects reticulocytes based on the first fluorescence intensity and the first forward scattered light intensity. The process of step S806 is described using FIG. 20. The information of each particle contained in the measurement data are plotted in a two-dimensional space in which the first fluorescence intensity is represented on one coordinate axis and the first forward scattered light intensity is represented on the other coordinate axis, as shown in FIG. 20. In FIG. 20 the reticulocytes are distributed in region 950. The information of region 950 is recorded on the hard disk 304 as the reticulocyte detection region. The CPU 301 detects the particles appearing in region 950 as reticulocytes.

Refer again to FIG. 19. In step S807, the CPU 301 extracts the particles for which the second fluorescence intensity is above a predetermined threshold from the particles groups designated reticulocytes as reticulocytes which produce auto-fluorescence (referred to as "auto-fluorescent reticulocytes" below), counts the auto-fluorescent reticulocytes, and designates the result as the auto-fluorescent reticulocyte count. That is, the CPU 301 identifies the individual auto-fluorescent reticulocytes by the detected intensity of the auto-fluorescence, and counts the auto-fluorescent reticulocytes. Specifically, the CPU 301 sets a detection region in which the second fluorescence intensity is above the threshold value in a two-dimensional space wherein the second fluorescence intensity is represented on one coordinate axis and the second forward scattered light intensity is represented on the other coordinate axis, and detects the particles appearing in this detection region as auto-fluorescent reticulocytes. The auto-fluorescence produced by the reticulocytes of a patient with iron deficiency anemia is detected as a high value compared to the auto-fluorescence produced by the reticulocytes of a person which does not have iron deficiency anemia. In the present embodiment, the auto-fluorescence produced by reticulocytes of a person who does not have iron deficiency anemia cannot be detected because it is hidden by noise. In the present embodiment, reticulocytes having detected second auto-fluorescence above the threshold value are designated as auto-fluorescent reticulocytes, and reticulocytes having no detected second auto-fluorescence above the threshold value are defined as non-autofluorescent reticulocytes. A detection region in which the second fluorescence intensity is above the threshold value is set in a two-dimensional space wherein the second fluorescence intensity is represented on one coordinate axis and the second forward scattered light intensity is represented on the other coordinate axis, and the particles appearing in this detection region are detected as auto-fluorescent reticulocytes. In this case the second forward scattered light detecting part 942 can be omitted.

In step S808, the CPU 301 calculates the auto-fluorescent reticulocyte count relative to the number of reticulocytes (referred to as "second auto-fluorescence ratio" below) as the reticulocyte auto-fluorescence information. In step S809, the CPU 301 compares the second fluorescence ratio with a predetermined third threshold value, and determines the possibility of iron deficiency anemia. The second auto-fluorescence ratio is information obtained by individually detecting the auto-fluorescence produced by each reticulocyte.

Figure 21:
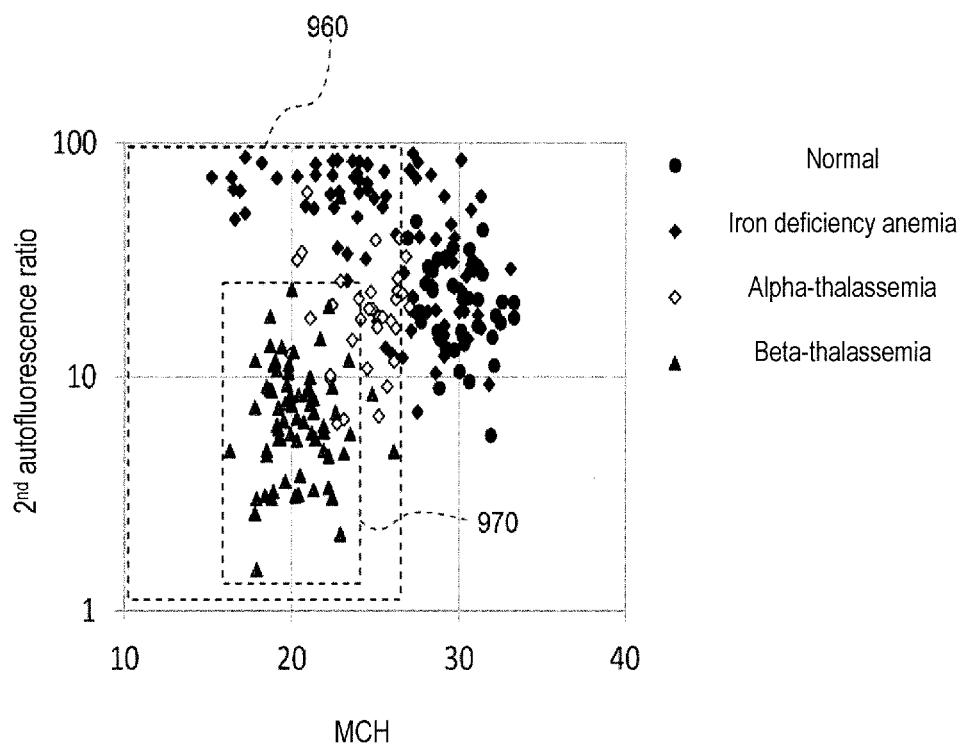
FIG. 21 shows the relationship of the ratios of the number of reticulocytes which produce auto-fluorescence relative to the total number of reticulocytes, and the MCH in the blood sample.

Refer to FIG. 21. In FIG. 21, the vertical axis represents the second auto-fluorescence ratio and the horizontal axis represents MCH. Each point in FIG. 21 represents a blood sample. Region 960 in FIG. 21 is the range of high possibility of microcytic anemia. Most iron deficiency anemia samples and thalassemia samples appear in region 960. Among the blood samples in region 960, the iron deficiency anemia samples have a larger second fluorescence ratio than the thalassemia samples. The majority of iron deficiency anemia samples are distributed in the range in which the second fluorescence ratio is 30% or greater. The majority of thalassemia samples are distributed in the range in which the second fluorescence ratio is less than 30%. The majority of normal samples are distributed in the range in which the second fluorescence ratio is less than 30%. From the above it is understood that iron deficiency anemia can be differentiated from thalassemia and normal samples by using the second auto-fluorescence ratio. The possibility of iron deficiency anemia also can be determined using the fluorescing reticulocyte count. In this case iron deficiency anemia also can be differentiated from thalassemia and normal samples.

Reticulocytes of patients with iron deficiency anemia include abundant protoporphin. Reticulocytes lose subcellular organelles after two to three days and become mature red blood cells. In the process of reticulocytes changing to red blood cells, most of the protoporphin in the reticulocytes is thought to disappear together with the subcellular organelles. Therefore, the amount of protoporphin contained in the reticulocytes is abundant compared to red blood cells.

Reticulocytes of healthy persons and patients with thalassemia have a low protoporphin content. Accordingly, the amount of protoporphin contained in reticulocytes of patients with iron deficiency anemia is markedly greater compared to reticulocytes of healthy persons or patients with thalassemia. Accordingly, the possibility of iron deficiency anemia can be determined with good accuracy using the second fluorescence ratio, than by using the red blood cell auto-fluorescence ratio.

Figure 22:
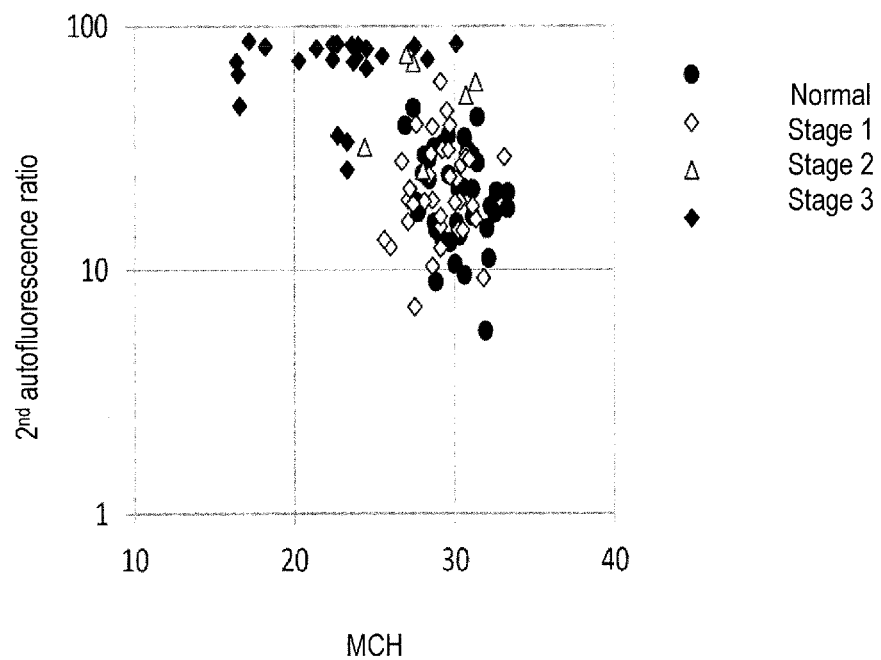
FIG. 22 is a graph showing the relationship of the ratios of the number of reticulocytes which produce auto-fluorescence relative to the total number of reticulocytes, and the stage of iron deficiency anemia.

Refer to FIG. 22. In FIG. 22, the vertical axis represents the second auto-fluorescence ratio and the horizontal axis represents MCH. Each point in FIG. 22 represents a blood sample. In FIG. 22, normal samples and samples of iron deficiency anemia from stage 1 through stage 3 are indicated by changing the type of point.

In FIG. 22, the normal samples have a second auto-fluorescence ratio of 10% or higher but no more than 30%, and MCH is mostly distributed within the range of 25 or higher but no more than 35. Stage 1 samples have a second auto-fluorescence ratio of 10% or higher but no more than 40%, and MCH is mostly distributed within the range of 25 or higher but no more than 35. That is, stage 1 samples are distributed in approximately the same range as the normal samples. Stage 2 samples have a second auto-fluorescence ratio of 30% or higher but no more than 80%, and MCH is mostly distributed within the range of 22 or higher but no more than 32. Stage 3 samples have a second auto-fluorescence ratio of 50% or higher but no more than 100%, and MCH is mostly distributed within the range of 15 or higher but no more than 30. When comparing FIGS. 22 and 8, normal samples have a higher second auto-fluorescence ratio compared to the auto-fluorescence ratio of red blood cells whatever the stage of iron deficiency anemia. It is understood that the second auto-fluorescence ratio of stage 2 and 3 samples is markedly larger than the auto-fluorescence ratio of red blood cells.

The majority of reticulocytes collected from patients with iron deficiency anemia are thought to contain abundant protoporphin. On the other hand, even though reticulocytes sometimes contain abundant protoporphin, most of the protoporphin disappears in the process of changing to a red blood cell, and red blood cells are considered to have a low protoporphin content. Red blood cells with a low protoporphin content produce weak auto-fluorescence and are not detected as auto-fluorescent red blood cells. Since such red blood cells are present at a constant proportion, the second auto-fluorescence ratio of patients with iron deficiency anemia is thought to be greater than the auto-fluorescence ratio of red blood cells.

Since reticulocytes of patients with iron deficiency anemia contain abundant protoporphin compared to red blood cells, the amount of light from auto-fluorescence produced by reticulocytes is greater than the amount of light from auto-fluorescence produced by red blood cells. Accordingly, the auto-fluorescence detection accuracy is higher for reticulocytes than red blood cells. The second auto-fluorescence ratio therefore has higher accuracy than the auto-fluorescence ratio of red blood cells. The accuracy of making determination regarding anemia can be improved by using this second auto-fluorescence ratio rather than the auto-fluorescence ratio of red blood cells.

From FIG. 22, it is understood that at least stage 3 iron deficiency anemia samples can be differentiated from normal samples if the second threshold value is set from 30% or higher but no more than approximately 50%.

Refer again to FIG. 19. When the second auto-fluorescence ratio is equal to or greater than the third threshold value, the CPU 301 sets the second flag to [1] in step S810, ends the second measurement data analysis process, and returns the process to the main routine. When the second auto-fluorescence ratio is less than the third threshold value, the CPU 301 compares the second auto-fluorescence ratio with a predetermined fourth threshold value and determines the possibility of beta-thalassemia in step S811. The fourth threshold value is smaller than the third threshold value.

Refer again to FIG. 21. The second auto-fluorescence ratio of beta-thalassemia samples is smaller than the second auto-fluorescence ratio of normal samples and alpha-thalassemia samples. Specifically, beta-thalassemia samples have a second auto-fluorescence ratio mostly distributed in the range below 20%. The amount of protoporphin contained in reticulocytes of patients with beta-thalassemia is markedly small compared to the reticulocytes of patients with iron deficiency anemia. Accordingly, the possibility of beta-thalassemia can be determined with good accuracy using the second fluorescence ratio, than by using the red blood cell auto-fluorescence ratio.

Refer again to FIG. 19. When the second auto-fluorescence ratio is less than the fourth threshold value, the CPU 301 sets the third flag to [1] in step S812, ends the second measurement data analysis process, and returns the process to the main routine. When the auto-fluorescence ratio is equal to or greater than the fourth threshold value, the CPU 301 ends the second measurement data analysis process and returns the process to the main routine.

When the second auto-fluorescence ratio is less than the fourth threshold value, it is also possible to determine a high possibility of thalassemia including alpha-thalassemia and beta-thalassemia. When the second auto-fluorescence ratio is less than the third threshold value, it also is possible to determine a high possibility of thalassemia without using the fourth threshold value. In a two-dimensional coordinate space in which one coordinate axis is designated for the second auto-fluorescence ratio and the other coordinate axis is designated for MCH, the determination area 970 of beta-thalassemia is stipulated as shown in FIG. 21, and it is possible to determine a high possibility of beta-thalassemia when the second auto-fluorescence ratio and MCH enter the determination area 970.

A configuration also may use the second auto-fluorescence ratio to determine iron deficiency anemia without performing a determination related to thalassemia. A configuration also may use the second auto-fluorescence ratio to determine thalassemia without performing a determination related to iron deficiency anemia.

Refer again to FIG. 16B. In step S620, the CPU 301 displays the analysis results on the output unit 310, and the process ends. The analysis results include red blood cell count, hemoglobin concentration, MCH, auto-fluorescent red blood cell count, and auto-fluorescence ratio of red blood cells, auto-fluorescent reticulocyte count, and second auto-fluorescence ratio of each measurement result, and reference information for diagnosis. When the first flag is set at [1], the reference information includes information indicating the high possibility of microcytic anemia. When the second flag is set at [1], the reference information includes information indicating the high possibility of iron deficiency anemia. When the third flag is set at [1], the reference information includes information indicating the high possibility of beta-thalassemia.

Figure 23:
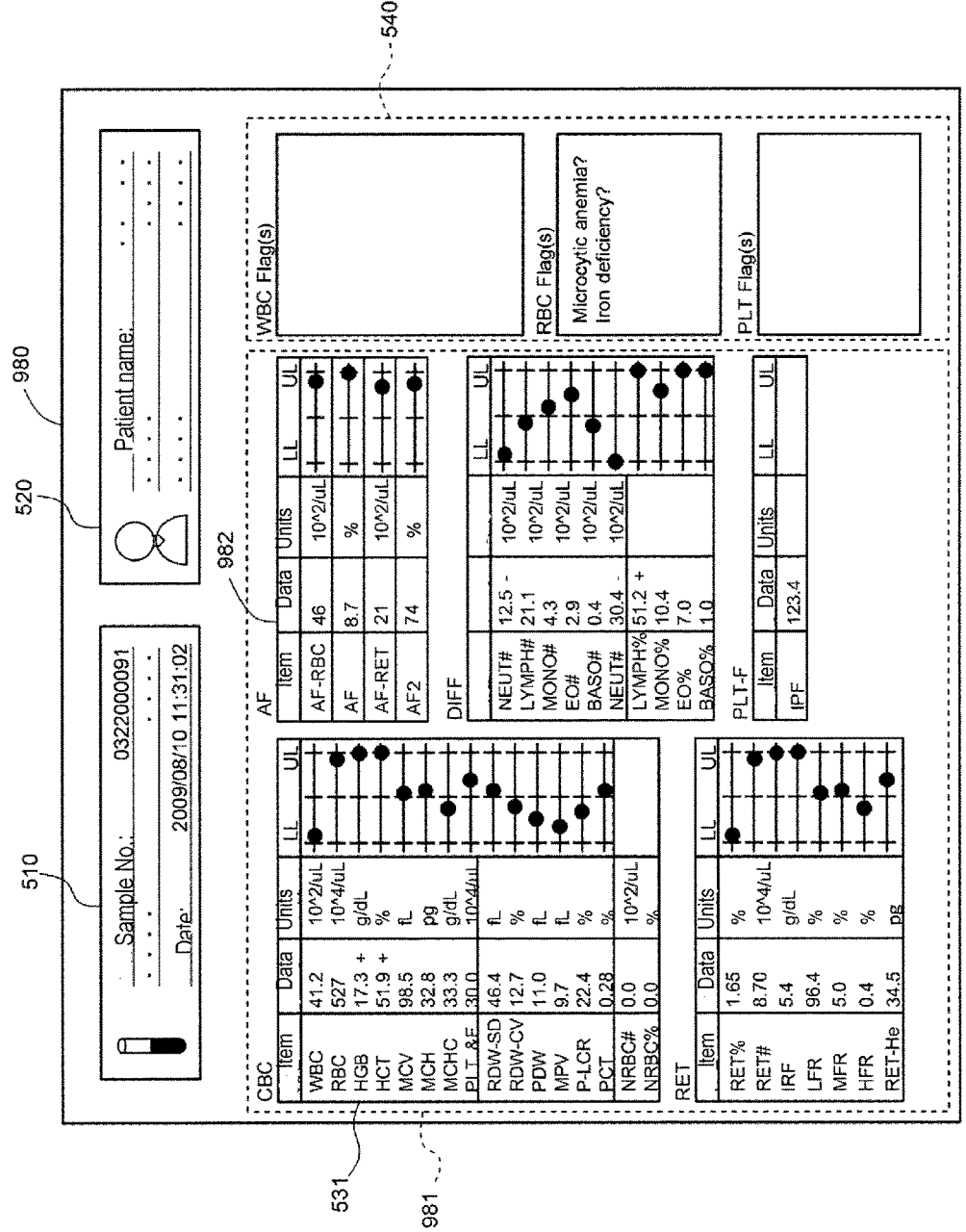
FIG. 23 shows a display example of analysis results in the fourth embodiment.

The displayed analysis results are described below referring to FIG. 23. An analysis results screen 980 is displayed on the output unit 310. The analysis results screen 980 has a sample information display region 510, patient information display region 520, measurement results display region 981, and reference information display region 540. The measurement results display region 981 has a CBC item display region 531, and auto-fluorescence item display region 982. The sample information display region 510, patient information display region 520, CBC item display region 531, and reference information display region 540 are identical to the first embodiment, and the description is omitted.

Measurement values of measurement items related to auto-fluorescence are displayed in the auto-fluorescence item display region 982. Measurement items displayed in the measurement item display region 982 include the auto-fluorescent red blood cell count (AF-RBC), red blood cell auto-fluorescence ratio (AF), auto-fluorescent reticulocyte count (AF-RET), and second auto-fluorescence ratio (AF2) measurement values.

A configuration also may be employed to automatically measure reticulocyte auto-fluorescence and make a determination regarding anemia when reticulocyte measurement is required based on results of the first measurement data analysis process. A configuration also may be employed to detect reticulocyte auto-fluorescence and make a determination regarding anemia without detecting red blood cell auto-fluorescence beforehand. Specifically, it is configurable to execute only the operations of step S611 and steps S612 through S619 without executing the operations of steps S602 through S611. For example, in the case of a sample collected from a patient with suspected anemia, reticulocyte auto-fluorescence may be detected and a determination regarding anemia may be made using the reticulocyte auto-fluorescence information without detecting red blood cell auto-fluorescence. In this way it is possible to make determination regarding anemia with high accuracy while minimizing the consumption of sample by directly detecting reticulocyte auto-fluorescence without detecting red blood cell auto-fluorescence. This configuration would be particularly useful in regions with an abundance of anemia patients such as Southeast Asia. When red blood cell auto-fluorescence is measured and analysis results are obtained which indicate a high possibility of thalassemia, the user may manually operate the blood analyzer to measure reticulocyte auto-fluorescence and make a detailed determination regarding thalassemia.

Fifth Embodiment

In the fifth embodiment, a blood analyzer configured to monitor the status of iron deficiency anemia of a patient is described.

Blood Analyzer Structure

The structure of the blood analyzer of the fifth embodiment is identical to the structure of the blood analyzer of the fourth embodiment, like structural elements are denoted by like reference numbers, and the description is omitted.

Operation of the Blood Analyzer

Figure 24:
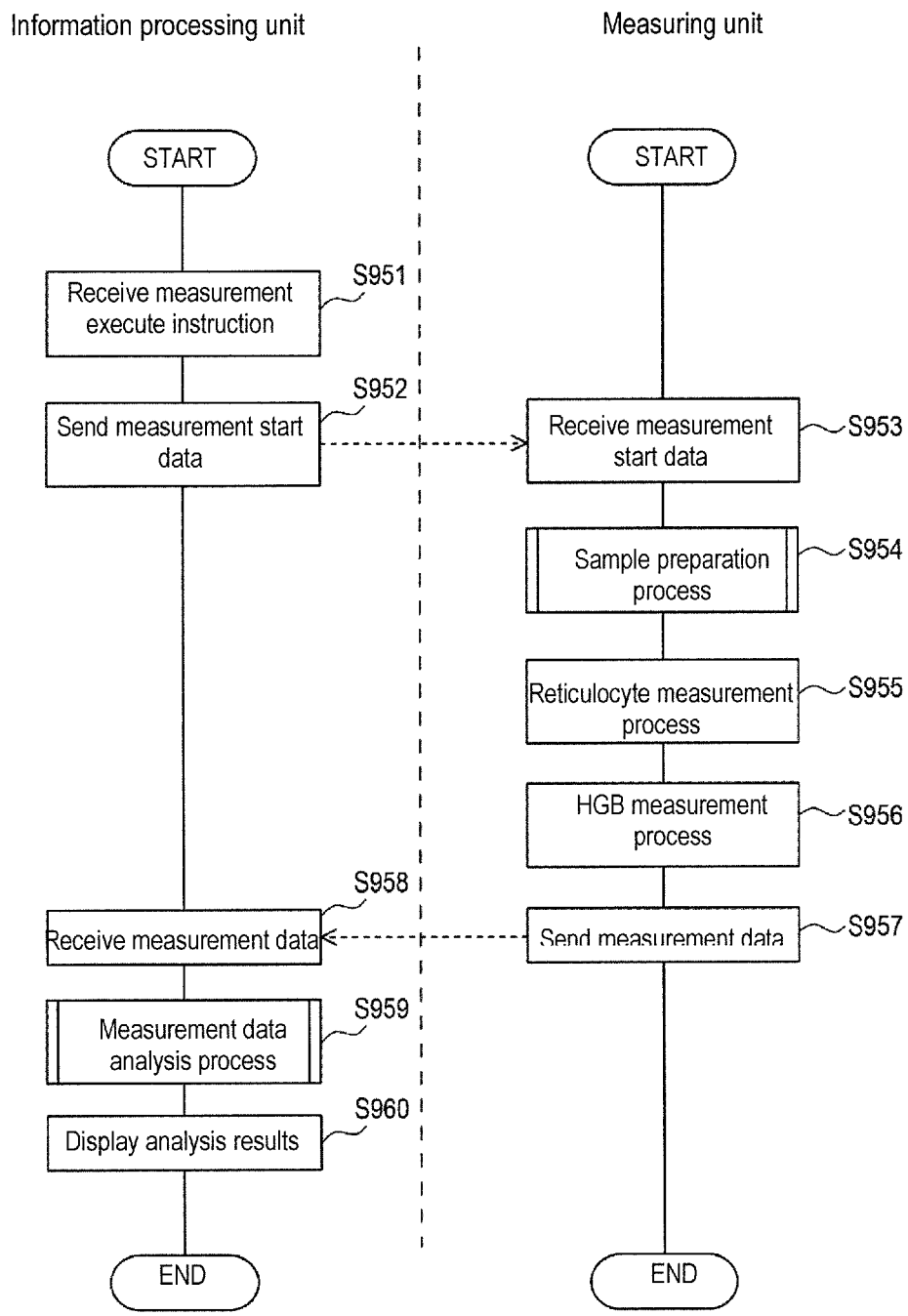
FIG. 24 is a flow chart showing the flow of the operation performed by the blood analyzer of a fifth embodiment.

The blood analyzer of the fifth embodiment does not perform the operations of steps S602 through S610 among the operations of the blood analyzer of the fourth embodiment. That is, the blood analyzer detects reticulocyte auto-fluorescence and does not detect red blood cell auto-fluorescence. The operation of the blood analyzer 100 is described referring to FIG. 24.

In step S951, the CPU 301 of the information processing unit 3 receives the instruction to execute a measurement from the user through the input unit 309. When the instruction to execute a measurement is received, the CPU 301 sends instruction data to start the measurement to the measuring unit 200 in step S952. In step S953, the measuring unit 200 receives the instruction data. The microcomputer 82 executes the measurement sample preparation process in step S954, executes the reticulocyte measurement process in step S955, and executes the HGB measurement process in step S956. Since the process in steps S954 through S956 are identical to the process of steps S614 through S616 of the fourth embodiment, the description is omitted.

After the HGB measurement process, the microcomputer 82 sends the measurement data containing each characteristic parameter to the information processing unit 3 in step S957 and the process ends.

When the information processing unit 3 receives the measurement data in step S958, the CPU 301 executes the measurement data analysis process to generate blood sample analysis results and stores the analysis results in the hard disk 304 in step S959.

Figure 25:
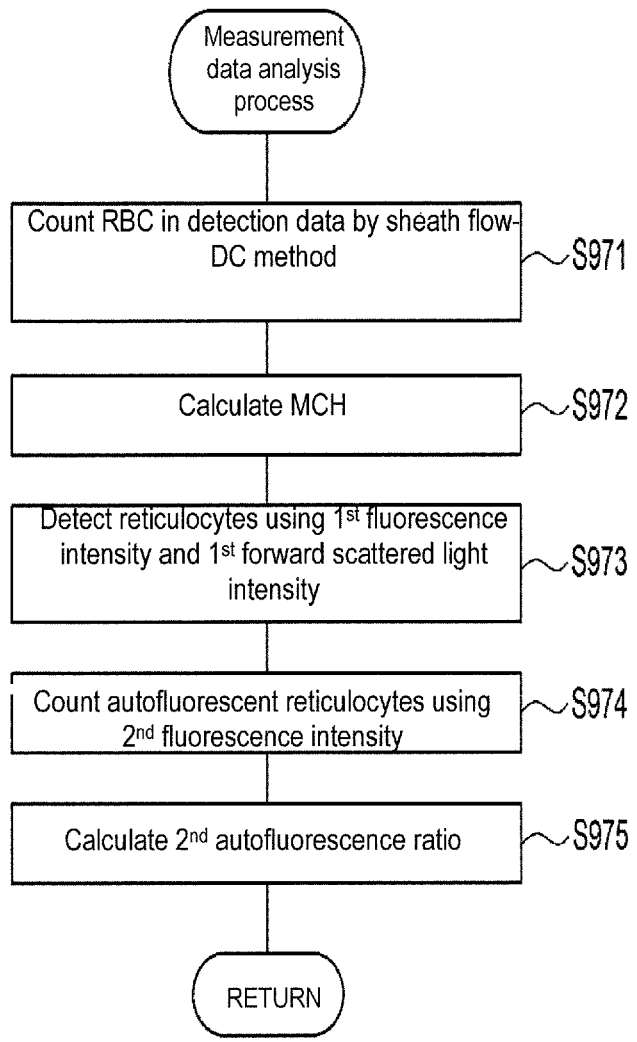
FIG. 25 is a flow chart showing the sequence of the measurement data analyzing process of the fifth embodiment.

Refer to FIG. 25. When the measurement data analysis process is started, the CPU 301 first counts the red blood cells in step S971 using the red blood cell detection data obtained by the sheath flow-DC method.

The CPU 301 then calculates the MCH from the red blood cell count and hemoglobin concentration in step S972.

In step S973, the CPU 301 detects reticulocytes based on the first fluorescence intensity and the first forward scattered light intensity. The process in step S973 is identical to step S806 of the fourth embodiment.

In step S974, the CPU 301 extracts particles for which the second fluorescence intensity is equal to or greater than a predetermined threshold value from among the particle group designated as reticulocytes as auto-fluorescent reticulocytes, and counts the auto-fluorescent reticulocytes.

The CPU 301 calculates the second auto-fluorescence ratio in step S975. When the process of step S975 ends, the CPU 301 ends the measurement data analysis process, and returns the process to the main routine.

The second auto-fluorescence ratio increases as the degree of iron deficiency anemia becomes more severe, and the second auto-fluorescence ratio decreases as the degree of iron deficiency anemia moderates. Accordingly, the degree of iron deficiency anemia can be estimated by the value of the second auto-fluorescence ratio.

Refer again to FIG. 24. In step S960, the CPU 301 displays the analysis results on the output unit 310, and the process ends.

Figure 26:
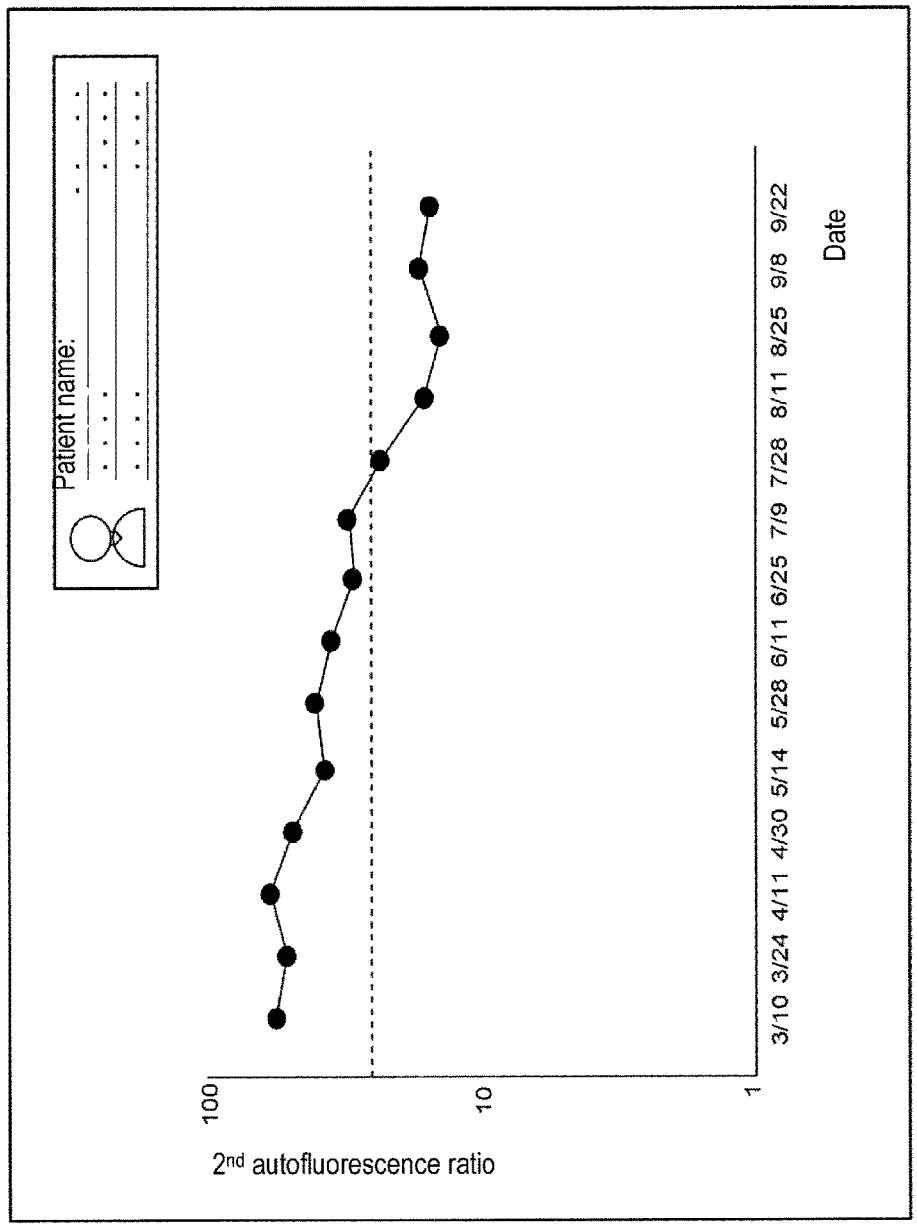
FIG. 26 shows a display example of analysis results in the fifth embodiment.

The displayed analysis results are described below referring to FIG. 26. The CPU 301 displays a time series graph of the second auto-fluorescence ratio measured on several days for the same patient as analysis results. In FIG. 26, the horizontal axis represents the date and the vertical axis represents the second auto-fluorescence ratio. Analysis results for a patient receiving treatment for iron deficiency anemia are shown in FIG. 26.

In the example of FIG. 26, the second auto-fluorescence ratio decreases over time. The dashed line in FIG. 26 is baseline of determination related to iron deficiency anemia. The user can determine a high possibility of iron deficiency anemia when the second auto-fluorescence ratio is above the baseline, and determine a low possibility of iron deficiency anemia when the second auto-fluorescence ratio is below the baseline. In the example shown in FIG. 26, the second auto-fluorescence ratio decreases over time from a position above the baseline, and ultimately the second auto-fluorescence ratio is positioned near the baseline indicating the iron deficiency anemia is improving.

The life of a red blood cell is approximately 120 days. Although the auto-fluorescence detected from new red blood cells reflects the current condition regarding the anemia of the patient, whereas the auto-fluorescence detected from old red blood cells reflects the condition related to the anemia of the patient at the time the red blood cell was produced. That is, the auto-fluorescence of a red blood cell reflects the condition regarding the anemia of the patient up to approximately 120 days ago. Therefore, although the auto-fluorescence of red blood cells is suited for understanding the long-term trend of the patient's iron deficiency anemia, it does not necessarily accurately reflect the current condition of the patient's iron deficiency anemia.

On the other hand, a reticulocyte changes to a red blood cell within two to three days after it is produced. Therefore, the auto-fluorescence detected from reticulocytes reflects the current condition of the patient's anemia. That is, the second auto-fluorescence ratio reflects the current status of the iron deficiency anemia of the patient. The user therefore can more accurately monitor the status of the iron deficiency anemia of the patient by displaying the second auto-fluorescence ratio in time series.

A single blood analyzer can perform not only the function of monitoring the status of iron deficiency anemia using a flow cytometric method, but also perform the function of making a determination regarding anemia using the flow cytometric method as described in the fourth embodiment.

Other Embodiments

Although the first through fifth embodiments have been described in terms of configurations for making determinations regarding anemia using an auto-fluorescence ratio, the present invention is not limited to these configurations. It is possible to make determinations regarding anemia by using information relating to detected auto-fluorescent red blood cells because red blood cell auto-fluorescence is connected to anemia. Specifically, a high possibility of iron deficiency anemia can be determined using the auto-fluorescent red blood cell count as the auto-fluorescence information when the number of red blood cells producing auto-fluorescence exceeds a predetermined first threshold value. A high possibility of thalassemia also can be determined when there is a high possibility of microcytic anemia and the number of red blood cells producing auto-fluorescence is less than a predetermined second threshold value. A high possibility of iron deficiency anemia also can be determined when the ratio of red blood cells producing auto-fluorescence relative to the number of red blood cells which do not produce auto-fluorescence is greater than a predetermined first threshold value by using the ratio of red blood cells producing auto-fluorescence relative to the number of red blood cells which do not produce auto-fluorescence as the auto-fluorescence information. A high possibility of thalassemia also can be determined when there is a high possibility of microcytic anemia and the ratio of red blood cells producing auto-fluorescence relative to the number of red blood cells which do not produce auto-fluorescence is less than a predetermined second threshold value. A high possibility of iron deficiency anemia also can be determined when the total fluorescence intensity of the auto-fluorescent red blood cells is greater than a predetermined first threshold value by using the total fluorescence intensity of the auto-fluorescent red blood cells as the auto-fluorescence information. A high possibility of thalassemia also can be determined when there is a high possibility of microcytic anemia and the total fluorescence intensity of the auto-fluorescent red blood cells is less than a predetermined second threshold value. The possibility of anemia also can be determined by dividing the distribution of fluorescence intensity of auto-fluorescent red blood cells used as auto-fluorescence information, that is, the region in which fluorescence intensity appears, into, for example, "low," medium," "high" from the lowest fluorescence intensity based on the percentage of auto-fluorescent red blood cells appearing in the respective areas. In this case, a high possibility of iron deficiency anemia can be determined when, for example, the percentage of auto-fluorescent red blood cells appearing in the "high" area exceeds a predetermined first threshold value. A high possibility of thalassemia also can be determined when there is a high possibility of microcytic anemia and, for example, the percentage of auto-fluorescent red blood cells appearing in the "low" area exceeds a predetermined second threshold value. A high possibility of iron deficiency anemia also can be determined when the peak value of the fluorescence intensity of the auto-fluorescent red blood cells is greater than a predetermined first threshold value, by using the peak value of the fluorescence intensity of the auto-fluorescent red blood cells as information related to the distribution of the fluorescence intensity of the auto-fluorescent red blood cells. A high possibility of thalassemia also can be determined when there is a high possibility of microcytic anemia and the peak value of fluorescence intensity of the auto-fluorescent red blood cells is less than a predetermined second threshold value. A determination regarding anemia also can be made by detecting the auto-fluorescence of reticulocytes and obtaining information regarding the auto-fluorescent reticulocytes as per above, and using this information regarding auto-fluorescent reticulocytes. In each of the above embodiments, the first threshold value is greater than the second threshold value. The first threshold value and the second threshold value also may be the same.

Although the fifth embodiment is described in terms of a configuration for irradiating a measurement sample with blue light having a central wavelength of 405 nm and detecting the auto-fluorescence, the present invention is not limited to this configuration. The wavelength range of the blue light used to detect auto-fluorescence may be 400 nm or greater but not more than 435 nm.

Although the first, second, fourth, and fifth embodiments are described in terms of a configuration in which the fluorescence detecting unit has a sensitive wavelength range of 400 nm or greater but no more than 1000 nm, the present invention is not limited to this configuration. The fluorescence detecting unit also may have another sensitive wavelength range insofar as the wavelength is within a range of 600 nm or greater but no more than 700 nm.

Although the first, third, and fourth embodiments are described in terms of a configuration which makes a determination regarding microcytic anemia using MCH, the present invention is not limited to this configuration. A determination regarding microcytic anemia also can be made using MCV or MCHC.

Although the first, third, and fourth embodiments are described in terms of a configuration for making a determination regarding microcytic anemia, making a determination regarding iron deficiency anemia, and making a determination regarding thalassemia, the present invention is not limited to this configuration. A configuration for making a determination regarding iron deficiency anemia and making a determination regarding thalassemia by detecting auto-fluorescence without making a determination regarding microcytic anemia is also possible. A configuration for making a determination regarding iron deficiency anemia and making a determination regarding thalassemia by detecting auto-fluorescence without making a determination regarding microcytic anemia is also possible.

What is claimed is:

1. A blood analyzer, comprising:
    a light source configured to irradiate the prepared specimen with light of a wavelength selected to excite auto-fluorescence out of red blood cells in the prepared specimen;
    a fluorescent light detector configured to detect the auto-fluorescence excited out by the light source from at least some red blood cells in the prepared specimen and output a signal that carries an auto-fluorescent measurement indicative of an amount of red blood cells exciting auto-fluorescence in the prepared specimen;
    a light detector configured to sense a respective blood cell in the prepared specimen and output a signal that carries a size measurement indicative of a size of a respective blood cell in the prepared specimen;
    an information processor programmed to execute an anemia classifying algorithm for evaluating the auto-fluorescence measurements from the fluorescent detector to classify the prepared specimen into a category of iron-deficiency anemia or a category of thalassemia, wherein the anemia classifying algorithm being executed to:
    from the size measurements from the cell detector, count total red blood cells;
    from the auto-fluorescence measurements from the light detector, count the at least some red blood cells in the prepared specimen that emit the auto-fluorescence;
    calculate a ratio of a count of the at least some red blood cells in the prepared specimen that emit the auto-fluorescence relative to a count of the total red blood cells; and
    classify the prepared specimen into a category of iron-deficiency anemia or a category of thalassemia, based on the ratio.

2. The blood analyzer of claim 1, wherein the fluorescent light detector is further configured to individually detect the auto-fluorescence from each red blood cell in the measurement sample.

3. The blood analyzer of claim 1, wherein the information processor is configured to make a determination regarding iron deficiency anemia based on the auto-fluorescence information.

4. The blood analyzer of claim 1, wherein the information processor is configured to make a determination regarding thalassernia based on the auto-fluorescence information.

5. The blood analyzer of claim 1, wherein the information processor is programmed to further calculate a breadth of distribution of fluorescent light intensity of red blood cells which produce the auto-fluorescence.

6. The blood analyzer of claim 3, wherein the auto-fluorescence information is a total of fluorescent light values of the red blood cells which produce the auto-fluorescence, and
    the information processor is programmed to further make a determination of a high possibility of iron deficiency anemia in response that the total of the fluorescent light values of red blood cells producing the auto-fluorescence exceeds a predetermined threshold value.

7. The blood analyzer of claim 1, wherein the information processor is programmed to further make a determination regarding anemia based on information obtained based on the auto-fluorescence information and the count of red blood cells and hemoglobin concentration of blood collected from a human.

8. The blood analyzer of claim 1, further comprising:
    an output unit;
    wherein the information processor is programmed to further output information regarding anemia to the output unit based on the auto-fluorescence information.

9. The blood analyzer of claim 1, further comprising:
    a sample preparation unit configured to prepare a measurement sample without hemolysis or staining blood.

10. The blood analyzer of claim 1, further comprising:
    a sample preparation unit configured to prepare a measurement sample by mixing a blood sample and a staining reagent containing a fluorescent dye for specifically staining reticulocytes;

wherein the light source unit comprises a first light source configured to irradiate stained reticulocytes with a first light for producing fluorescence at a first wavelength, and a second light source for irradiating red blood cells with a second light for producing the auto-fluorescence of a second wavelength which is different from the first wavelength;

wherein the fluorescent light detecting unit comprises a first fluorescent light detector configured to detect fluorescent light of a first wavelength produced from the reticulocytes irradiated by the light of the first wavelength, and a second fluorescent light detector configured to detect auto-fluorescence of the second wavelength produced from the red blood cells irradiated by the second light;

the information processing unit is further configured to obtain auto-fluorescence information related to reticulocytes which produce auto-fluorescence based on the fluorescent light of the first wavelength detected by the first fluorescent light detector and the auto-fluorescence of the second wavelength detected by the second fluorescent light detector, and make a determination related to anemia based on the auto-fluorescence information related to reticulocytes and the auto-fluorescence of the second wavelength.

11. The blood analyzer of claim 10, wherein the auto-fluorescence information related to reticulocytes represents the ratio of a count of reticulocytes producing the auto-fluorescence relative to a total count of reticulocytes.

12. The blood analyzer of claim 1, wherein the light source unit is configured to irradiate the measurement sample with light in a wavelength range of 400 nm or greater but no more than 435 nm; and the fluorescent light detecting unit is configured to detect light in a wavelength range of 600 nm or greater but no more than 700 nm as auto-fluorescence.

13. The blood analyzer of claim 1, further comprising:
a flow cell for flowing measurement samples;
the light source unit is configured to irradiate light on the measurement samples flowing through the flow cell;
wherein the fluorescent light detecting unit is configured to detect auto-fluorescence produced from red blood cells flowing through the flow cell.

14. A diagnostic support method for anemia, the method comprising:
providing a specimen prepared to measure a respective red blood cell in the prepared specimen;
irradiating the prepared specimen with light of a wavelength selected to excite auto-fluorescence out of red blood cells in the prepared specimen;
detecting the auto-fluorescence excited out from at least some red blood cells in the prepared specimen and outputting a signal that carries an auto-fluorescence measurement indicative of an amount of red blood cells exciting auto-fluorescence in the prepared specimen;
sensing a respective blood cell in the prepared specimen and outputting a signal that carries a size measurement indicative of a size of a respective blood cell in the prepared specimen;
from the size measurements, counting total red blood cells;
from the auto-fluorescence measurements, counting the at least some red blood cells in the prepared specimen that emit the auto-fluorescence;

calculating a ratio of a count of the at least some red blood cells that emit the auto-fluorescence relative to a count of the total red blood cells in the prepared specimen; and
classify the prepared specimen into a category of iron-deficiency anemia or a category of thalassemia, based on the ratio.

15. A non-transitory storage medium storing a computer program executed by a computer to:
provide a specimen prepared to measure a respective red blood cell in the prepared specimen;
irradiate the prepared specimen with light of a wavelength selected to excite auto-fluorescence out of red blood cells in the prepared specimen;
detect the auto-fluorescence excited out from at least some red blood cells in the prepared specimen and output a signal that carries an auto-fluorescence measurement indicative of an amount of red blood cells exciting auto-fluorescence;
sense a respective blood cell in the prepared specimen and output a signal that carries a size measurement indicative of a size of a respective blood cell in the prepared specimen;
from the size measurements, count total red blood cells;
from the auto-fluorescence measurements, count the at least some red blood cells in the prepared specimen that emit the auto-fluorescence;
calculate a ratio of a count of the at least some red blood cells that emit the auto-fluorescence relative to a count of the total red blood cells in the prepared specimen; and
classify the prepared specimen into a category of iron-deficiency anemia or a category of thalassemia, based on the ratio.

16. The blood analyzer according to claim 1, wherein the prepared specimen comprises first and second types of prepared specimen, the first and second types of prepared specimen being withdrawn from a single patient and prepared differently, the first type of prepared specimen being optically interrogated to measure an amount of the red blood cells exciting auto-fluorescence in the first type of prepared specimen,
the blood analyzer further comprises an HGB detector configured to interrogate red blood cells in the second type of prepared specimen and output a signal carrying HGB measurements indicative of a hemoglobin concentration of the second type of prepared specimen,
the information processor further configured to execute a MCH algorithm for calculating a mean corpuscular hemoglobin (MCH) of the second type of prepared specimen from the HGB measurements and evaluating the calculated MCH with a predetermined MCH threshold to classify the prepared specimen into a category of microcytic anemia or a category of non-anemia, depending on whether or not the calculated MCH is in excess of the predetermined MCH threshold, and
the information processor further configured to execute the anemia classifying algorithm in response to classification by the MCH algorithm of the prepared specimen into the category of microcytic anemia, whereas not executing the anemia classifying algorithm in response to classification by the MCH algorithm of the prepared specimen into the category of non-anemia.

17. The blood analyzer according to claim 16, wherein the cell detector is either (a) a light detector configured to optically detect light of the selected wavelength scattered by blood cells in the prepared specimen and output the signal that carries the size measurement indicative of a size of a respective blood cell in the prepared specimen or (b) a sheath flow-DC detector configured to electrically detect blood cells in the prepared specimen and output the signal that carries the size measurement indicative of a size of a respective blood cell in the prepared specimen.

18. The blood analyzer according to claim 16, wherein the prepared specimen comprises a smear specimen,
the light source comprises a first and second types of light source, the first type of light source being configured to radiate light of the selected wavelength to excite protoporphilyn to emit auto-fluorescence therefrom, the second type light source being configured to radiate light of a wavelength that is different from the selected wavelength and selected to be absorbed by red blood cells but not by white blood cells,
the light detector comprises first and second types of light detector, the first type of light detector being configured to detect the auto-fluorescence excited out by the first type of light source from the protoporphilyn included in the at least some red blood cells in the smear specimen and output a first image that shows an amount of the protoporphilyn contained in a respective at least some red blood cells in the smear specimen, the second type of light detector being configured to detect the light from the second type of light source and output a second image that shows the total red blood cells in the smear specimen,
the information processor further configured to execute a MCH algorithm for determining, from the second image a mean corpuscular hemoglobin (MCH) of the smear specimen and evaluating the determined MCH with a predetermined MCH threshold to classify the spear specimen into a category of microcytic anemia or a category of non-anemia, depending on whether or not the calculated MCH is in excess of the predetermined MCH threshold, and
the information processor further configured to execute the anemia classifying algorithm in response to classification by the MCH algorithm of the prepared specimen into the category of microcytic anemia, whereas not executing the anemia classifying algorithm in response to classification by the MCH algorithm of the prepared specimen into the category of non-anemia, wherein the anemia classifying algorithm is executed to acquire a differential between the first and second images and from the acquired differential, count red blood cells in the smear specimen that each contain a detectable amount of protoporphilyn.

19. The blood analyzer according to claim 16, wherein:
the prepared specimen comprises a RET specimen in which reticulocytes are stained, the prepared specimen and the RET specimen being withdrawn from a single patient;
the light source comprises a first and second types of light source,
the first type of light source being configured to irradiate the RET specimen with light of the selected wavelength to excite the auto-fluorescent out of protoporphilyn contained in any stained reticulocytes in the RET specimen, wherein the first type of light source is used to irradiate the prepared specimen with light of the selected wavelength to excite auto-fluorescence out of protoporphilyn contained in any red blood cells in the prepared specimen, and
the second type light source being configured to irradiate the RET specimen with light of a wavelength that is different from the selected wavelength and selected to excite RET fluorescence out of a respective stained reticulocyte in the RET specimen,
the light detector comprises first and second types of light detector, and
the first type of light detector being configured to detect the auto-fluorescence excited out by the first type of light source from protoporphilyn included in at least some stained reticulocytes in the RET specimen and output a signal that carries a RET protoporphilyn measurement indicative of an amount of protoporphilyn contained in a respective at least some stained reticulocytes in the RET specimen, wherein the first type of light detector is used to detect the auto-fluorescence excited out by the first type of light source from the protoporphilyn included in at least some red blood cells in the prepared specimen, and
the second type of light detector being configured to detect the light from the second type of light source scattered by the stained reticulocytes in the RET specimen and output a signal that carries a RET size measurement indicative of a size of a respective stained reticulocyte in the RET specimen; and
the information processor is programmed to execute a RET classifying algorithm for evaluating the RET protoporphilyn measurements from the first type of light detector to classify the RET specimen into a category of iron-deficiency anemia or a category of thalassemia, wherein the anemia classifying algorithm being executed to:
from the RET size measurements from the second type of light detector, count total stained reticulocytes in the RET specimen;
from the RET protoporphilyn measurements from the first type of light detector, count the at least some reticulocytes in the RET specimen that emit the auto-fluorescence;
calculate a ratio of a count of the at least some reticulocytes in the RET specimen that emit the auto-fluorescence relative to a count of the total stained reticulocytes present in the RET specimen; and
compare the ratio with a predetermined RET protoporphilyn threshold to classify the RET specimen into a category of iron-deficiency anemia or a category of thalassemia, depending on whether or not the ratio is in excess of the predetermined RET protoporphilyn threshold.

* * * * *